(12) United States Patent
Striker et al.

(10) Patent No.: US 8,871,741 B2
(45) Date of Patent: Oct. 28, 2014

(54) INHIBITION OF TNF-α INDUCED ACTIVATION OF NFKB BY PENTOSAN POLYSULFATE

(75) Inventors: Gary E. Striker, New York, NY (US); Helen Vlassara, New York, NY (US); Feng Zheng, Middle Village, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 13/522,441

(22) PCT Filed: Jan. 14, 2011

(86) PCT No.: PCT/US2011/021429
§ 371 (c)(1),
(2), (4) Date: Oct. 5, 2012

(87) PCT Pub. No.: WO2011/088418
PCT Pub. Date: Jul. 21, 2011

(65) Prior Publication Data
US 2013/0143837 A1    Jun. 6, 2013

Related U.S. Application Data

(60) Provisional application No. 61/295,409, filed on Jan. 15, 2010.

(51) Int. Cl.
*A61K 31/70*    (2006.01)
*A61K 31/737*   (2006.01)
*C12Q 1/02*     (2006.01)

(52) U.S. Cl.
CPC .............. *A61K 31/737* (2013.01); *C12Q 1/025* (2013.01)
USPC ........................................................... 514/54

(58) Field of Classification Search
USPC ............................................................. 514/54
See application file for complete search history.

(56) References Cited

U.S. PATENT DOCUMENTS 6,828,309 B2 * 12/2004 Striker ........................... 514/54
2003/0170745 A1   9/2003 Pereira
2007/0243218 A1  10/2007 Ellinghuysen et al.

OTHER PUBLICATIONS

Elliot et al., "Pentosan polysulfate descreases proliferation and net extracellular matrix production in mouse mesangial cells"; J. Am. Soc. Nephrol.; vol. 10(1); pp. 62-68 (1999).
Zhang et al., "Role of TNF-alpha in vascular dysfunction"; Clin. Sci; vol. 118(3); pp. 219-230 (2009).
Sadhukhan et al., "Sodium pentosan polysulfate reduces urothelial responses to inflammatory stimuli via an indirect mechanism"; J. Urol.; vol. 168(1); pp. 289-292 (2002).
International Search Report mailed Aug. 3, 2011, which issued in corresponding International Application No. PCT/US2011/021429.

* cited by examiner

*Primary Examiner* — Elli Peselev
(74) *Attorney, Agent, or Firm* — Fish & Richardson P.C.

(57) ABSTRACT

Oral pentosan polysulfate (PPS) compositions treat diseases such as diabetes, inflammation, atherosclerosis. The compositions are also effective in reducing matrix metalloproteinases (MMPs).

3 Claims, 21 Drawing Sheets

A

B

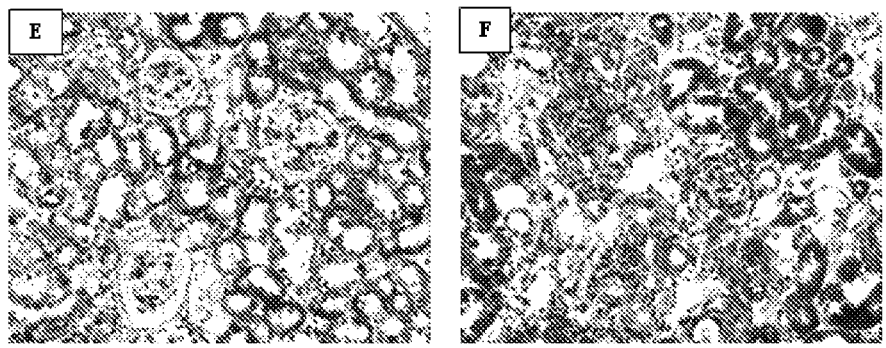
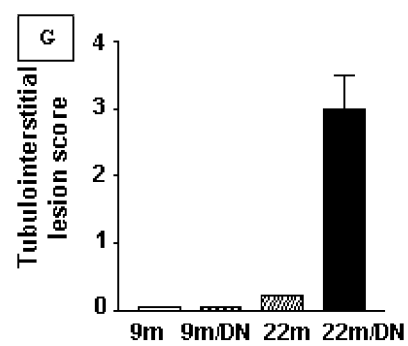
FIGURES 9E-9G

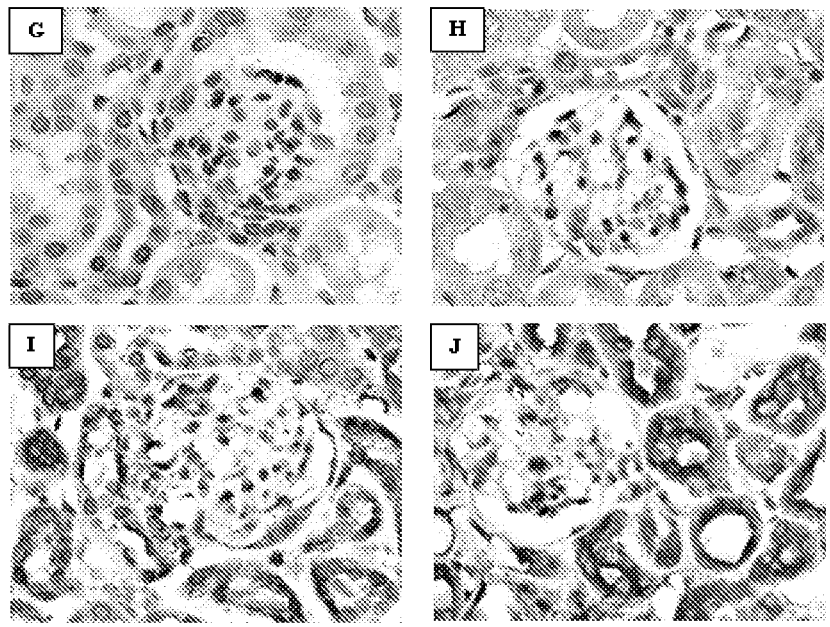
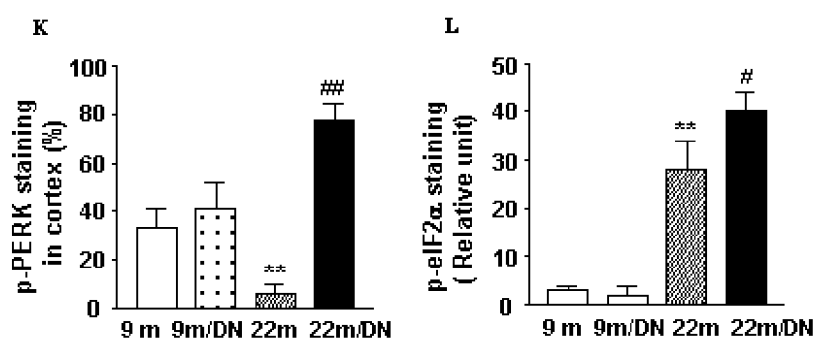
FIGURES 12G-12L

INHIBITION OF TNF-α INDUCED ACTIVATION OF NFKB BY PENTOSAN POLYSULFATE

CROSS REFERENCE TO RELATED APPLICATION

This application is the U.S. National Phase application under 35 U.S.C. §371 of International Patent Application No. PCT/US2011/021429, filed Jan. 14, 2011, and claims priority to U.S. provisional application No. 61/295,409, filed Jan. 15, 2010, each of which is hereby incorporated herein by reference in its entirety. The International Application published in English on Jul. 21, 2011 as WO 2011/088418 under PCT Article 21(2).

STATEMENT REGARDING FEDERALLY SPONSORED RESEARCH

This invention was made with U.S. government support under grant number R01AG19366-7A1 awarded by the National Institutes of Health. The U.S. government has certain rights in the invention.

REFERENCE TO SEQUENCE LISTING

Pursuant to 37 C.F.R. 1.821(c), a sequence listing is submitted herewith via EFS-Web as an ASCII compliant text file named "Sequencelisting.TXT" that was created on Jan. 8, 2013, and has a size of 3557 bytes. The content of the aforementioned file named "Sequencelisting.TXT" is hereby incorporated by reference in its entirety

FIELD OF THE INVENTION

The invention is related to the field of therapeutics that inhibit nuclear factor-κB (NF-κB) induced activation by tumor necrosis alpha (TNFα).

BACKGROUND

Heparin and heparin-like molecules have been proposed as therapeutic agents in the atherosclerotic process (Engelberg H. *Pharmacol Rev.* 1996; 48: 327-351). Besides their well-known anticoagulant action, these molecules regulate leukocyte-blood vessel interactions and infiltration of monocytes/macrophages. The accumulation of macrophage-derived foam cells in atherosclerotic plaques may influence vascular remodeling and plaque rupture, processes implicated in unstable angina and acute myocardial infarction.

The prevalence of chronic and end-stage kidney disease increases with age. According to the Fourth US National Health and Nutrition Examination Survey (NHANES IV, 1999-2004), 23.8% of individuals over 60 years of age and 37.8% of individuals over 70 years of age had a moderate to severe decline of renal function. Reduced renal function in aging could be a significant health issue because it is a known risk factor for kidney failure and cardiovascular disease. The cause of declining renal function in some aging persons is not clear. A process of natural biological aging may play an important role since 13% of older individuals had reduced renal function in the absence of obvious disease such as diabetes and hypertension. Excessive oxidative stress (OS) is critically involved in the overall aging process. There is a strong correlation between renal function and the levels of OS in aging. Additionally, the levels of OS are increased in the kidneys of old animals. Interventions that reduce OS, i.e., caloric restriction and genetic manipulations to overexpress antioxidants, prolong life span and prevent aging related pathologic changes in kidney of animals. Thus, OS may also play an essential role in kidney aging. The presence of intervening disease such as diabetes may accelerate kidney aging process because of the addition of hyperglycemia-induced OS. Hyperglycemia stimulates mitochondrial reactive oxygen species (ROS) generation and increases the formation of advanced glycation end-products (AGEs) intracellularly and extracellularly. Since AGEs also promote OS, a cycle of AGE formation and ROS generation may ensue.

In addition to a close association with elevated OS, the reduction of renal function in aging is also strongly correlated with a state of chronic inflammation, characterized by increased serum levels of tumor necrosis factor α (TNF-α) and its soluble receptors. Since inflammation is a key component of all forms of progressive chronic kidney diseases including diabetic nephropathy, inflammation may be another important contributor to increased renal lesions in aging mice after the induction of diabetes.

SUMMARY

This Summary is provided to present a summary of the invention to briefly indicate the nature and substance of the invention. It is submitted with the understanding that it will not be used to interpret or limit the scope or meaning of the claims.

The invention is directed to compositions and methods for the inhibition of nuclear factor-κB (NF-κB) induced activation by tumor necrosis alpha (TNFα).

In certain aspects, the invention is directed to treatments of diabetes, inflammatory diseases or other diseases.

In certain aspects, the invention is directed to preventing or treating a disease or disorder associated with tumor necrosis factor-α (TNFα) induction of nuclear factor-κB (NF-κB) activation, by administering a patient a therapeutically effective dose of pentosan polysulfate (PPS).

In certain aspects, the invention is directed to preventing or treating atherosclerosis in a patient by a therapeutically effective dose of pentosan polysulfate (PPS).

In certain aspects, the invention is directed to modulating metalloproteinase (MMP) activity in vivo by administering a therapeutically effective dose of pentosan polysulfate (PPS).

In certain aspects, the invention is directed to treating acute or chronic inflammatory disease in a patient by administering a therapeutically effective dose of pentosan polysulfate (PPS).

In certain aspects, the invention is directed to methods of modulating metalloproteinase activity in vitro by contacting a cell with at least about 0.0001 μg/ml of pentosan polysulfate.

In certain aspects, the invention is directed to screening for candidate therapeutic agents by contacting a biological sample with a candidate agent, assaying for expression profiles or changes in expression of at least one nucleic acid sequence or encoded products thereof in presence or absence of a candidate agent.

In certain aspects, the invention is directed to oral pentosan polysulfate (PPS) compositions for the treatment of diseases such as diabetes, inflammation, and atherosclerosis. The compositions are also effective in reducing matrix metalloproteinases (MMPs).

In certain aspects, the invention is directed to compounds and compositions useful for carrying out any of the aforementioned aspects.

Other aspects are described infra.

BRIEF DESCRIPTION OF THE DRAWINGS

FIG. 1A: HC-diet plus tap water. FIG. 1B: HC-diet for 75 days, on day 45 PPS was added to the drinking water and continued for the remaining 30 days. FIG. 1C: En Fasse analysis of the atherosclerotic lesions, expressed as percent lesion area on the surface of the whole intima (surface area of lesion/surface area of the whole intima). White bars: WHHL rabbits fed a HC-diet for 75 days; Diagonal hatched bars: WHHL rabbits fed a HC-diet for 75 days, on day 45 PPS was added to the drinking water and continued for the remaining 30 days. *P<0.05.

FIG. 2A: HC-diet plus tap water. FIG. 2B: HC-diet for 75 days, on day 45 PPS was added to the drinking water and continued for the remaining 30 days. FIG. 2C: I/M ratio of aortic cross sections. White bars: WHHL rabbits fed a HC-diet for 45 days; Black bars: WHHL rabbits fed a HC-diet for 75 days; Diagonal hatched bars: WHHL rabbits fed a HC-diet for 75 days, on day 45 PPS was added to the drinking water and continued for the remaining 30 days. Quantification of atherosclerotic lesions was performed by computer-aided morphometric analysis in the aortic arch and the abdominal aorta, near to the origin of the renal arteries, as detailed in the Materials and Methods section. *P<0.05, **P<0.01.

FIG. 3A: HC-diet plus tap water. FIG. 3B: HC-diet for 75 days, on day 45 PPS was added to the drinking water and continued for the remaining 30 days. FIG. 3D: HC-diet plus tap water. FIG. 3E: HC-diet for 75 days, on day 45 PPS was added to the drinking water and continued for the remaining 30 days.

FIG. 4A: Representative zymography of extracts from aortas of WHHL rabbits fed a HC-diet. Lane 1: 45 days HC diet; Lane 2: 75 days HC diet; Lane 3: 75 days HC-diet, on day 45 PPS was added to the drinking water and continued for the remaining 30 days. FIG. 4B: Quantification of MMP activity in aortic extracts. White bars: WHHL rabbits fed a HC-diet for 45 days; Black bars: WHHL rabbits fed a HC-diet for 75 days; Diagonal hatched bars: WHHL rabbits fed a HC-diet for 75 days, on day 45 PPS was added to the drinking water and continued for the remaining 30 days. (n=3 experiments, ***P<0.005).

FIG. 5A shows representative reverse zymographic analysis of extracts from aortas of WHHL rabbits fed a HC-diet. Lane 1: standard; Lane 2: 45 days HC diet; Lane 3: 75 days HC diet; Lane 4: 75 days HC-diet, on day 45 PPS was added to the drinking water and continued for the remaining 30 days. B. Graphic representation of three experiments. White bars: WHHL rabbits fed a HC-diet for 45 days; Black bars: WHHL rabbits fed a HC-diet for 75 days; Diagonal hatched bars: WHHL rabbits fed a HC-diet for 75 days, on day 45 PPS was added to the drinking water and continued for the remaining 30 days. (n=3 experiments, *P<0.05, **P<0.01).

FIG. 6A shows a representative zymographic analysis of supernatants from U937 cells. Lane 1: unstimulated; Lane 2: unstimulated, pretreated with heparin (100 µg/ml); Lane 3: treated with 10 ng/ml TNF-α; Lane 4: treatment with 10 ng/ml TNFα following pretreatment with 100 µg/ml PPS; Lane 5: treatment with 10 ng/ml TNF-α, following pretreatment with 100 µg/ml heparin. FIG. 6B shows the quantification of MMP-2 activity in the supernatants of unstimulated U937 cells. Open bars=no treatment; Diagonal hatched bars=treatment with 100 µg/ml PPS. Data are expressed as percent of control (unstimulated U937 cells). Shown are mean and SEM of five independent experiments. **P<0.01. FIG. 6C shows the quantification of MMP-2 and MMP-9 activity in the supernatants of U937 cells stimulated with 10 ng/ml TNF-α. Open bars=no treatment; Diagonal hatched bars=treatment with 100 µg/ml PPS. Data are expressed as percent of control (10 ng/ml TNF-α stimulated U937 cells). Shown are mean and SEM of five independent experiments. *P<0.05, **P<0.01. FIG. 6D shows a representative zymographic analysis of supernatants from human peripheral blood-derived macrophages unstimulated (lanes 1 and 2) or stimulated with 10 ng/ml TNF-α (lanes 3 and 4). Lane 2 and 4: human peripheral blood-derived macrophages were pretreated with 100 µg/ml PPS. FIG. 6E shows the quantification of MMP-2 and MMP-9 activity in the supernatants of unstimulated human peripheral blood-derived macrophages, in the absence (open bars) or presence (diagonal hatched bars) of 100 µg/ml PPS, expressed as percent of control (unstimulated human peripheral blood-derived macrophages). Shown are mean and SEM of three independent experiments. *P<0.05, **P<0.01. FIG. 6F shows the quantification of MMP-2 and MMP-9 activity in the supernatants of human peripheral blood-derived macrophages stimulated with 10 ng/ml TNF-α, in the absence (open bars) or presence (diagonal hatched bars) of 100 µg/ml PPS, expressed as percent of control (10 ng/ml TNF-α stimulated human peripheral blood-derived macrophages). Shown are mean and SEM of three independent experiments. *P<0.05, **P<0.01.

FIG. 7A: 22 month-old (22 m) C57B6 female mice did not have significant albuminuria. Urinary albumin was modestly elevated in 9 month-old diabetic mice (9 m/DN). 22 month-old diabetic mice developed severe and progressive albuminuria (22 m/DN). *p<0.05, vs. 9 month-old non-diabetic mice (9 m); ##p<0.01, vs., 9 m/DN. FIG. 7B: The levels of albuminuria in 22 month-old mice after 4 months of hyperglycemia were 11-fold higher than in 9 month-old mice after 4 months of hyperglycemia. ##p<0.01.

FIG. 8A: 9 month-old mice: Normal glomeruli and tubulointerstitium (PAS×200). FIG. 8B: 9 month-old diabetic mice: Increased glomerular size and mesangial areas (PAS×200). FIG. 8C: 22 month-old mice: Increased glomerular size and minimal glomerulosclerosis (PAS×200). FIG. 8D: 22 month-old diabetic mice: Enlarged glomeruli with significant expansion of mesangial matrix (PAS×200). Bowman's capsule and tubular basement membranes are thickened. The width of arteriolar walls is increased (arrow). There is tubular atrophy and widened interstitial spaces. FIG. 8E: 22 month-old diabetic mice: The walls of afferent (upper arrow) and efferent (lower arrow) arterioles are thickened and filled with homogenous PAS positive hyalin material (PAS×400). FIG. 8F: Mesangial area quantitation: The mesangial area, expressed as a percentage of total glomerular area, was increased in the kidneys of both 9 month-old and 22 month-old diabetic mice, but it was more prominent in the kidneys of 22 month-old diabetic mice. *p<0.05, vs. 9 m. ##p<0.01, vs. 9 m/DN or 22 m.

FIGS. 9A-9G show changes in glomerular basement membrane, glomerular endothelial cell fenestrae and tubulointerstitium in 22 month-old diabetic mice. FIG. 9A: The glomerular basement membrane profiles and podocyte foot processes are relatively normal in 22 month-old mice (EM× 5000). FIG. 9B: The glomerular basement membranes are irregularly thickened and there is fusion of foot processes in 22 month-old diabetic mice (arrows, EM×5000). FIG. 9C: Quantitative analysis shows that the glomerular basement membrane width was significantly increased in 22 month-old diabetic mice. p<0.05, vs. 22 m. FIG. 9D: The amount of glomerular endothelial cell surfaces occupied by fenestratrae was reduced in 22 month-old diabetic mice. Data are expressed as the ratio of unfenestrated to fenestrated glomerular endothelium. P<0.01, vs. 22 m. FIG. 9E: Representative photomicrographs of Masson's trichrome stained sections of kidneys from 22 month-old non-diabetic mice. While blue staining (collagen) is increased in glomeruli, the tubulointerstitium is relatively normal (200×). FIG. 9F: Representative photograph of Masson's trichrome stained sections of kidney from a 22 month-old diabetic mouse. Severe tubulointerstitial lesions are characterized by tubular atrophy, interstitial fibrosis, and extensive inflammatory cell infiltration. FIG. 9G: Semi-quantitative assessment of tubulointerstitial lesions. No tubulointerstitial changes were present in the kidneys of 9 month-old non-diabetic (9 m) and 9 month-old diabetic (9 m/DN) mice. Tubulointerstitial lesions were minimal in 22 month-old non-diabetic mice, but were severe in the kidneys of 22 month-old diabetic mice (22 m/DN). The average score of tubulointerstitial lesions in 22 month-old diabetic mice was 3+.

FIG. 10A: Immunostaining for apoptotic cells in the kidneys of 22 month-old diabetic mice (×400). There are positively stained nuclei in tubular cells (arrows). FIG. 10B: Apoptotic cells were rarely seen in the kidneys of 9 month-old non-diabetic mice (9 m) and were only occasionally seen in the kidneys of 9 month-old diabetic (9 m/DN) and 22 month-old non-diabetic mice. There was a 6-fold increase in the number of apoptotic cells in the kidneys of 22 month-old diabetic mice (22 m/DN). **, p<0.01, vs. 22 m.

FIG. 11A: The kidney AGE content, as measured by competitive ELISA, is expressed as a ratio relative to protein concentrations (mg). AGE accumulation was increased in 9 month-old diabetic mice (9 m/DN) and in 22 month-old non-diabetic mice (22 m) and was further increased in kidneys of 22 month-old diabetic mice (22 m/DN). *p<0.01, vs. 9 month-old mice (9 m); #p<0.05, vs. 9 m/DN or 22 m. FIG. 11B: The levels of protein oxidation in 10 µg of protein from the kidneys of 9 month-old (9 m), 9 month-old diabetic (9 m/DN), 22 month-old (22 m), and 22 month-old diabetic mice (22 m/DN) were determined by western-blots using a anti-oxidized protein antibody. Representative gels of two animals from each group show that, while the bands of oxidized protein are visible in samples of the kidneys from 9 month-old mice (upper gel, 9 m, lane 1, 2), stronger bands with a similar pattern of proteins are seen in kidney samples from 9 month-old diabetic (upper gel, 9 m/DN, lane 3, 4) and 22 month-old mice (upper gel, 22 m, lane 5, 6). Protein oxidation is markedly increased in kidneys from 22 month-old diabetic mice (upper gel, 22 m/DN, lane 7, 8). Oxidized protein standards of different molecular weights are used as markers of protein size, and as a positive control for Western-blots. The lower panel shows the same gel stained with ponceau red prior to western-blotting with the anti-oxidized protein antibody. FIGS. 11C, 11D, 11E and 11F show the nitrotyrosine immunostaining of kidneys from 9 month-old (FIG. 11C, ×400), 9 month-old diabetic (FIG. 11D, ×400), 22 month-old (FIG. 11E, ×400), and 22 month-old diabetic mice (FIG. 11F, ×400). Little staining is present in 9 month-old non-diabetic kidneys (FIG. 11C) staining is clearly visible in glomeruli and tubules of 9 month-old diabetic kidneys (FIG. 11D). 22 month-old diabetic kidneys exhibit the strongest nitrotyrosine staining (FIG. 11F). MDA immunostaining in kidneys from 9 month-old (FIG. 11G, ×400), 9 month-old diabetic (FIG. 11H, ×400), 22 month-old (FIG. 11I, ×400), and 22 month-old diabetic mice (FIG. 11J, ×400). The staining of tubular cytoplasm is more intense in 9 month-22 month-old diabetic and 22 month-old non-diabetic (FIGS. 11H, 11I, ×400) than in 9 month-old non-diabetic mice (FIG. 11G, ×400) and further increased in 22 month-old diabetic kidney (FIG. 11J, ×400). The intensity of immunostaining was measured by a morphometry software and defined by an arbitrarily unit. Both nitrotyrosine (FIG. 11K) and MDA (FIG. 110 staining were increased in 9 month-old diabetic and 22 month-old non-diabetic kidneys compared to 9 month-old non-diabetic kidneys. The staining was further increased in 22 month-old diabetic kidneys. **p<0.01, vs., 9 month-old non-diabetic (9 m); #p<0.05, ##p<0.01, vs., 22 month-old non-diabetic (22 m).

FIGS. 12A-12L show ER stress in the kidneys of 22 month-old diabetic mice. FIG. 12A: mRNA levels of GRP78, a marker for ER stress, were higher in kidneys of 22 month-old diabetic mice (22 m/DN, p<0.01, vs., 22 month-old non-diabetic, 22 m). FIG. 12B: CHOP mRNA levels were elevated in 9 month-old diabetic (9 m/DN) and 22 month-old non-diabetic kidneys and further increased in 22 month-old diabetic kidneys. p<0.01, vs., 9 m; ##p<0.01, vs., 22 m. (FIGS. 12C, 12D, 12E, 12F). Immunostaining for phosphorylated PERK of kidneys from 9 month-old (FIG. 12C, ×500), 9 month-old diabetic (FIG. 12D, ×500), 22 month-old (FIG. 12E, ×500), and 22 month-old diabetic mice (FIG. 12F, ×500). Positive staining is seen in both glomeruli and tubules. Staining in 22 month-old non-diabetic kidney (FIG. 12E) is less strong than in 9 month-old non-diabetic kidneys (FIG. 12C). However, 22 month-old diabetic kidney (FIG. 12F) show the strongest staining among the groups. FIG. 12G: Quantitation of the percentage of cells in renal cortex that were stained positively for phosphorylated PERK showed that number of positive cells was decreased in 22 month-old non-diabetic (22 m) but increased in 22 month-old diabetic mice. p<0.01, vs., 9 month-old non-diabetic (9 m). ##p<0.01, vs., 22 month-old non-diabetic or 9 month-old diabetic (9 m/DN). FIGS. 12G, 12H, 12I, 12J, 12K: Immunostaining for phosphorylated eIF2α in kidneys from 9 month-old (FIG. 12G, ×500), 9 month-old diabetic (FIG. 12H, ×500), 22 month-old (FIG. 12I, ×500), and 22 month-old diabetic mice (FIG. 12J, ×500). Quantitation of p-PERK: p-PERK staining was decreased in 22 month-old non-diabetic mice compared to either 9 month-old non-diabetic or 9 month-old diabetic mice (FIG. 12L). The staining is most intense in the kidneys of 22 month-old non-diabetic and 22 month-old diabetic mice. **$p<0.01$, vs. 9 month-old non-diabetic (9 m). #$p<0.05$, vs. 22 month-old non-diabetic.

FIG. 13A: CHOP$^{-/-}$ proximal tubular cells were relatively resistant to ER stress-induced cell death. Proximal tubular cells from wild type and CHOP$^{-/-}$ mice were treated with increasing concentrations of tunicamycin (0.6-1.2 μg/ml) for 24 hours. The percentage of cell death was quantified. $p<0.01$, vs, CHOP$^{-/-}$ cells at the same dosage. FIG. 13B: hyperglycemia was induce in CHOP$^{-/-}$ and wild type mice by streptozotocin and mice were followed for 4 months. Urine albumin excretion was elevated in wild type diabetic mice but not in CHOP$^{-/-}$ diabetic mice. $p<0.01$, vs, CHOP$^{-/-}$ diabetic mice. FIG. 13C: Moderate expansion of mesangial areas is present in wild type diabetic mice while CHOP$^{-/-}$ diabetic glomeruli are nearly normal (FIG. 13D, PAS×200).

(FIG. 15B). Representative gels of TNFα and GAPDH mRNA levels of kidneys from 9 month-old (9 months, 9 m), 9 month-old diabetic (9 m/DN), 22 month-old (22 m), 22 month-old diabetic mice (22 m/DN), and 22 month-old diabetic mice treated with PPS (22 m/DN+PPS). TNFα mRNA expression was only found in the kidneys of 22 month-old diabetic (lane 1-5). The expression was absent in 22 month-old (lane 6, 7), 9 month-old (lane 8), and PPS treated 22 month-old diabetic mice (lane 9-14) even when the number of PCR cycles was increased to 40. cDNA obtained from mouse macrophages (Mϕ) was used as a positive control for PCR. (FIGS. 15C-15J). TNFα induced upregulation of proinflammatory molecules, which was largely blocked by PPS. Cells from a proximal tubular line were treated with PPS (200 μg/ml) for 1 hour before stimulating with TNFα (10 ng/ml) and RNA was collected 4 hours later. The mRNA levels in cells without TNFα stimulation (control) were arbitrarily defined as 1. TNFα treatment caused a 2-9 fold increase in mRNA expression of (FIG. 15C) MCP-1, (FIG. 15E) RANTES, (FIG. 15G) CXCL-1, (FIG. 15H) MIP-2, (FIG. 15I) ICAM-1, and (FIG. 15J) iNOS. Pretreatment with PPS largely prevented the stimulation by TNFα. Furthermore, PPS decreased TNFα stimulated (FIG. 15D) MCP-1 and (FIG. 15F) RANTES protein production by proximal tubular cells. $p<0.01$, vs. TNFα alone.

FIG. 16A: Phosphorylated IκB, total IκB, and β-actin levels were determined by western blot using a sequential gel. FIG. 16B: NF-κB transcription activity was determined by transfecting proximal tubular cells with a luciferase reporter in the presence or absence of an IKK or IκB cDNA. Data are expressed as a relative unit after correcting the luciferase by galactosidase activity. Some cells were treated with TNFα in the presence of PPS after transfection. FIG. 16C: Nuclear protein was isolated from proximal tubular cells one hour after treating cells with TNFα in the presence or absence of PPS. The binding of NF-κB protein to DNA was determined by a gel shift assay. Positive controls included macrophages treated with LPS and the presence of anti-p65 antibody in the reaction. NF-κB DNA binding activity is present in untreated proximal tubular cells (left lane). The activity is increased by TNFα and PPS nearly completely blocks TNFα-stimulated NF-κB DNA binding activity (right lane).

FIGS. 17A-17N: show that PPS treatment prevented the progression of kidney disease in 22 month-old diabetic mice. FIG. 17A: Urinary albumin excretion increased progressively in untreated 22 month-old diabetic mice (22 m/DN). PPS treatment (22 m/DN+PPS) reduced about 50% of increase in the albumin excretion rate. *$p<0.05$, **$p<0.01$, vs., 22 m/DN at the same time point. FIGS. 17B, 17C: While untreated 22 month-old diabetic mice exhibited severe glomerular and tubulointerstitial lesions (FIG. 17B), PPS treatment substantially reduced glomerular and tubulointerstitial lesions (FIG. 17C). Morphometric analysis showed that PPS treatment decreased mesangial area (FIG. 17D) the glomerular basement membrane width (FIG. 17E) and largely prevented the reduction of glomerular endothelial fenestrations in 22 month-old diabetic mice (FIG. 17F). An 80% reduction in tubulointerstitial lesions was found in PPS treated 22 month-old diabetic mice (FIG. 17G). *$p<0.05$, $P<0.01$, vs. 22 m/DN. FIG. 17L, treated). FIGS. 17M, 17N: A large number of cell nuclei stained positively for phosphorylated NF-κB (p65 (Ser276)) in untreated 22 month-old diabetic kidney (FIG. 17M). The number of positively stained nuclei was noticeably reduced in PPS treated kidney (FIG. 17N).

DETAILED DESCRIPTION

Figures 1A, 1B, 1C:
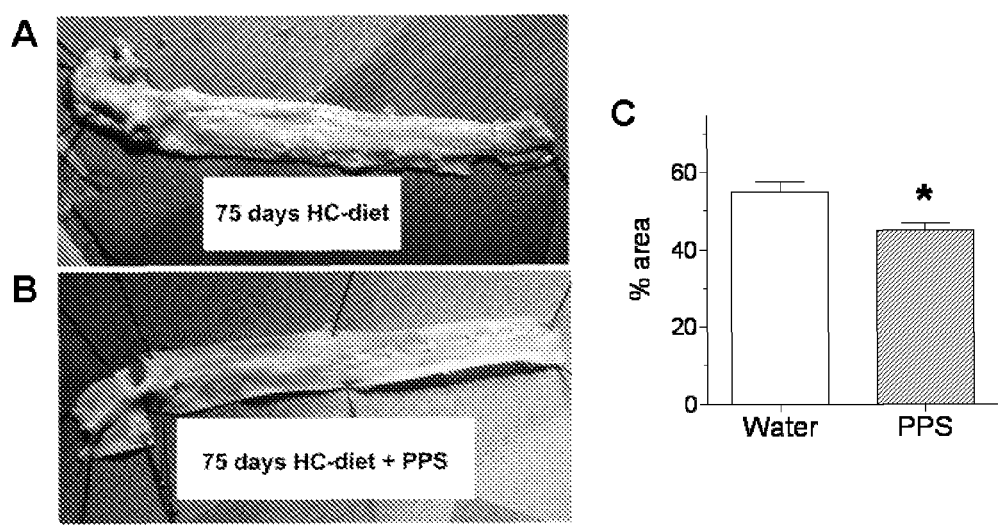
FIGS. 1A-1C show representative photographs of inner surface of aortas from WHHL rabbits fed a HC-diet for 75 days.

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In preferred embodiments, the genes or nucleic acid sequences are human.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "pentosan polysulfate" or "PPS" refers to a semi-synthetic sulfated polyanion composed of beta-D-xylopyranose residues with properties similar to heparin, with molecular weight ranges from 1500-5000. The compound is, for example, described in the Merck index, 10th edition, page 1025, Merck & Co, Inc, 1983. Other names used to describe this compound are, inter alia, xylan hydrogen sulfate; xylan polysulfate; CB 8061; Fibrase; Hemoclar.

The terms "biomolecule" or "markers" are used interchangeably herein and refer to DNA, RNA (including mRNA, rRNA, tRNA and tmRNA), nucleotides, nucleosides, analogs, polynucleotides, peptides and any combinations thereof.

Expression/amount of a gene, biomolecule, or biomarker in a first sample is at a level "greater than" the level in a second sample if the expression level/amount of the gene or biomarker in the first sample is at least about 1 time, 1.2 times, 1.5 times, 1.75 times, 2 times, 3 times, 4 times, 5 times, 6 times, 7 times, 8 times, 9 times, 10 times, 20 times, 30 times, the expression level/amount of the gene or biomarker in the second sample or a normal sample. Expression levels/amounts can be determined based on any suitable criterion known in the art, including but not limited to mRNA, cDNA, proteins, protein fragments and/or gene copy. Expression levels/amounts can be determined qualitatively and/or quantitatively.

By the term "modulate," it is meant that any of the mentioned activities, are, e.g., increased, enhanced, increased, agonized (acts as an agonist), promoted, decreased, reduced, suppressed blocked, or antagonized (acts as an antagonist). Modulation can increase activity more than 1-fold, 2-fold, 3-fold, 5-fold, 10-fold, 100-fold, etc., over baseline values. Modulation can also decrease its activity below baseline values.

"Biological samples" include solid and body fluid samples. Preferably, the sample is obtained from heart. However, the biological samples used in the present invention can include cells, protein or membrane extracts of cells, blood or biological fluids such as ascites fluid or brain fluid (e.g., cerebrospinal fluid). Examples of solid biological samples include, but are not limited to, samples taken from tissues of the central nervous system, bone, breast, kidney, cervix, endometrium, head/neck, gallbladder, parotid gland, prostate, pituitary gland, muscle, esophagus, stomach, small intestine, colon, liver, spleen, pancreas, thyroid, heart, lung, bladder, adipose, lymph node, uterus, ovary, adrenal gland, testes, tonsils and thymus. Examples of "body fluid samples" include, but are not limited to blood, serum, semen, prostate fluid, seminal fluid, urine, saliva, sputum, mucus, bone marrow, lymph, and tears.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Patient" or "subject" is intended to include human and non-human animals (e.g., mice, rats, rabbits, cats, dogs, livestock, and primates).

As used herein "a patient in need thereof" refers to any patient that is affected with a disorder characterized by, for example, an inflammatory disease or disorder. In one aspect of the invention "a patient in need thereof" refers to any patient that may have, or is at risk of having a disorder characterized by an inflammatory condition, including cancer.

As used herein, the term "test substance" or "candidate therapeutic agent" or "agent" are used interchangeably herein, and the terms are meant to encompass any molecule, chemical entity, composition, drug, therapeutic agent, chemotherapeutic agent, or biological agent capable of preventing, ameliorating, or treating a disease or other medical condition. The term includes small molecule compounds, antisense reagents, siRNA reagents, antibodies, enzymes, peptides organic or inorganic molecules, natural or synthetic compounds and the like. A test substance or agent can be assayed in accordance with the methods of the invention at any stage during clinical trials, during pre-trial testing, or following FDA-approval.

As used herein the phrase "diagnostic" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein the phrase "diagnosing" refers to classifying a disease or a symptom, determining a severity of the disease, monitoring disease progression, forecasting an outcome of a disease and/or prospects of recovery. The term "detecting" may also optionally encompass any of the above. Diagnosis of a disease according to the present invention can be effected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject, as described in greater detail below.

The term "correlating," as used in this specification refers to a process in which a set of examples of clinical inputs from subjects, and their corresponding outputs, such as detection of NF-κB induced activation by TNFα, are related to each other. This relationship can be determined by comparing such examples to examples from a control and/or disease-free population at a later point in time, and selecting those indicators which can differentiate between the two disease states as a function of time alone or in combination at a certain probability level. The selected markers, each at a certain level range which might be a simple threshold, are said to be correlative or associative with one of the disease states. Said correlated markers can be then be used for disease detection, diagnosis, prognosis and/or treatment outcome. Preferred methods of correlating, for example, markers is by performing marker selection as described in the examples section which follows. Methods can include a feature selection algorithm, statistics and classification by mapping functions described herein. A preferred probability level is a 3% chance, 5% chance, a 7% chance, a 10% chance, a 15% chance, a 20% chance, a 25% chance, a 30% chance, a 35% chance, a 40% chance, a 45% chance, a 50% chance, a 55% chance, a 60% chance, a 65% chance, a 70% chance, a 75% chance, a 80% chance, a 85% chance, a 90% chance, a 95% chance, and a 100% chance. Each of these values of probability is plus or minus 2% or less.

The terms "detecting", "detect", "identifying", "quantifying" includes assaying, quantitating, imaging or otherwise establishing the presence or absence of a molecule such as for example, NF-κB and the like, or assaying for, imaging, ascertaining, establishing, or otherwise determining the prognosis and/or diagnosis of, for example, inflammatory diseases or disorders.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

Pentosan Polysulfate and Compositions Thereof

Pentosan polysulfate (PPS, ELMIRON®), a heparinoid is essentially devoid of anticoagulant activity, reduces glomerular and tubulointerstitial fibrosis in mice with streptozotocin-induced diabetes (Striker G E, et al., *Kidney Int.* 1997; 63: S120-S123), in mice transgenic for bGH, and in rats with cyclosporin A nephropathy (Schwedler S B, et al., *Transplantation* 1999; 68: 1583-1588) or following ⅚ nephrectomy (Bobadilla N A, et al. *J Am Soc Nephrol* 2001; 12: 2080-2087). PPS decreases cell proliferation and production of collagen types I and IV in mouse mesangial cells and human vascular smooth muscle cells derived from vascular grafts and smooth muscle cells obtained from the prostate interstitium. On the other hand, PPS increases MMP-2 secretion and stimulates the production of tissue inhibitor of MMP (TIMP)-1 and the shedding of TIMP-3 from the surface of mesangial cells.

In a preferred embodiment, pentosan polysulfate (PPS) prevents, treats or reverses the progression of arthrosclerosis and established atherosclerotic lesions in vivo.

In another preferred embodiment, a method of preventing or treating a disease or disorder associated with tumor necrosis factor-α (TNFα) induction of nuclear factor-κB (NF-κB) activation, comprises administering to a patient in need thereof, a therapeutically effective dose of pentosan polysulfate (PPS). In preferred embodiments, the pentosan polysulfate is administered to a patient orally. The doses can be varied, fixed or combinations thereof. For example, depending on the diagnosis by a caregiver, the doses can be tailored for the specific patient and/or disease.

In preferred embodiments, a disease or disorder associated with TNFα induction of NF-κB comprises: chronic and acute inflammation, diabetic nephropathy, atherosclerosis, prostatic diseases or disorders, cardiovascular diseases or disorders, obesity, diabetes or combinations thereof.

In another preferred embodiment, a method of preventing or treating atherosclerosis in a patient comprises administering to a patient in need thereof, a therapeutically effective dose of pentosan polysulfate (PPS).

In a preferred embodiment, the pentosan polysulfate decreases atherosclerotic lesions or inhibits atherosclerotic lesion formation in a patient.

In another preferred embodiment, oral administration of the pentosan polysulfate inhibits monocytic infiltration into atherosclerotic plaques.

In another preferred embodiment, a method of modulating metalloproteinase (MMP) activity in vivo, comprises administering to a patient in need thereof, a therapeutically effective dose of pentosan polysulfate (PPS). Preferably, the pentosan polysulfate (PPS) is administered to a patient orally.

In another preferred embodiment, the pentosan polysulfate increases concentrations of tissue inhibitors of metalloproteinases (TIMP) in cells and tissues of patients.

In another preferred embodiment, a method of modulating metalloproteinase activity in vitro comprises contacting a cell with at least about 0.0001 µg/ml of pentosan polysulfate.

In another preferred embodiment, a method of treating acute or chronic inflammatory disease in a patient comprises administering to a patient in need thereof, a therapeutically effective dose of pentosan polysulfate (PPS). In a preferred embodiment, the pentosan polysulfate (PPS) is administered to a patient orally.

In another preferred embodiment, an acute or chronic inflammatory disease comprises: asthma, cancer, atherosclerosis, ischaemic heart disease, autoimmune diseases, chronic inflammation, chronic prostatitis, glomerulonephritis, hypersensitivities, inflammatory bowel diseases, pelvic inflammatory disease, reperfusion injury, rheumatoid arthritis, transplant rejection, vasculitis, allergic rhinitis, allergic dermatitis, allergic conjunctivitis, or combinations thereof.

In a preferred embodiment, a method of treating rheumatoid arthritis (RA) in a patient, comprises administering to a patient in need thereof, a therapeutically effective dose of pentosan polysulfate (PPS). In a preferred embodiment, the pentosan polysulfate (PPS) is administered to a patient orally.

RA has several special features that differentiate it from other types of arthritis. For example, RA generally occurs in a symmetrical pattern—if one knee or hand is involved, the other one is also. The disease often affects the wrist joints and the finger joints closest to the hand. RA usually first affects the small joints of the hands and feet, but may also involve the wrists, elbows, ankles and knees. It can also affect other parts of the body besides the joints. In addition, patients with the disease may have fatigue, occasional fever, and a general sense of not feeling well (malaise).

Another distinct feature of RA is the variance between individuals. For some, it lasts only a few months or a year or two and subsides without causing any noticeable damage. Other people have mild or moderate disease, with periods of worsening symptoms (flares) and periods in which they feel better (remissions). In severe cases, the disease is chronically active most of the time, lasting for many years, and leading to serious joint damage and disability.

RA encompasses a number of disease subtypes, such as Felty's syndrome, seronegative RA, "classical" RA, progressive and/or relapsing RA, and RA with vasculitis. Some experts classify the disease into type 1 or type 2. Type 1, the less common form, lasts a few months at most and leaves no permanent disability. Type 2 is chronic and lasts for years, sometimes for life.

In another preferred embodiment, a method of treating kidney disease or disorders in a patient, comprises administering to a patient in need thereof, a therapeutically effective dose of pentosan polysulfate (PPS). In a preferred embodiment, the pentosan polysulfate (PPS) is administered to a patient orally.

"Kidney disease" as used herein includes any malfunction of the kidney. Kidney disease may be identified by the presence of intact or modified albumin in the urine. Preferably, an early diagnosis of the kidney disease may be made by detecting the presence of modified protein in the urine, or an increase in the modified protein in the urine over time.

As used herein, "kidney disorder" refers to any pathologic disease or condition of the kidney including, for example, those diseases and conditions considered in Comprehensive Clinical Nephrology, 2nd Edition, edited by Richard J Johnson and John Feehally, Mosby, 2003, which is incorporated herein by reference in its entirety.

Diagnosis of a kidney disease or disorder also includes indices of kidney function including, for example, patient signs and symptoms, tests of general kidney function, for example, serum creatinine and blood urea nitrogen (BUN), or urinalysis, or tests of specific disorders of the kidney, for example, kidney biopsy, urine RNA levels, urine DNA levels, and other urinary markers.

Candidate Therapeutic Agents:

In a preferred embodiment, methods (also referred to herein as "screening assays") are provided for identifying modulators, i.e., candidate or test compounds or agents (e.g., proteins, peptides, peptidomimetics, peptoids, small molecules, analogues or other drugs) which modulate NF-κB expression, function, activity, or associated molecular pathways thereof. Compounds thus identified can be used to treat diseases such as for example, inflammation, diabetic nephropathy etc.

In another preferred embodiment, a method of screening for candidate therapeutic agents comprises contacting a biological sample with a candidate agent; assaying for expression profiles or changes in expression of at least one nucleic acid sequence or encoded products thereof in the presence or absence of a candidate agent. A biological sample can be of any type, such as for example, oligonucleotides, polynucleotides, polypeptides, peptides, cells, fluids, or tissues.

In one embodiment, a candidate agent is screened by a chip-based assay wherein the biochip comprises one or more biomarkers. Examples of biomarkers comprise MCP-1, CXCL-1, MIP-2, RANTES, ICAM-1, iNOS, VCAM-1, NF-κB, TNFα, variants, fragments, mutants, isoforms, derivatives, variants or combinations thereof.

In one embodiment, a candidate agent modulates expression of at least one marker molecule, such as for example, NF-κB in a cell based assay. The NF-κB can be, for example, an oligonucleotide, polynucleotide, polypeptide, peptide, variant, fragment or combinations thereof. In another preferred embodiment, the assay is a cell-based assay wherein a cell is contacted with a candidate agent and the expression profile induced by a candidate agent is correlated with expression profiles of nuclear factor-κB activation by tumor necrosis factor-α. In preferred embodiments, the expression profile induced by a candidate agent is correlated with expression profiles of markers comprising: MCP-1, CXCL-1, MIP-2, RANTES, ICAM-1, iNOS, VCAM-1, NF-κB, or TNFα.

In another preferred embodiment, a high-throughput screening assay (HTS) screening assay is used to screen a diverse library of member compounds. The "compounds" or "candidate therapeutic agents" or "candidate agents" can be any organic, inorganic, small molecule, protein, antibody, aptamer, nucleic acid molecule, or synthetic compound.

In another embodiment, the invention provides assays for screening candidate or test compounds that bind to or modulate an activity of Nf-κB protein or polypeptide or a biologically active portion thereof, mutants or fragments, or fusion proteins thereof. Other examples are biomarkers such as for example, MCP-1, CXCL-1, MIP-2, RANTES, ICAM-1, iNOS, VCAM-1 or TNFα. The biomarkers include, for example, oligonucleotides, polynucleotides, polypeptides, peptides, proteins, variants, fragments, derivatives, isoforms, alleles, or combinations thereof, of for example, MCP-1, CXCL-1, MIP-2, RANTES, ICAM-1, iNOS, VCAM-1 or TNFα. Determining the ability of the test compound to modulate the activity, expression etc, can be accomplished by various methods, including for example, fluorescence, protein assays, blots and the like. The cell, for example, can be of mammalian origin, e.g., human.

Candidate therapeutic agents include numerous chemical classes, though typically they are organic compounds including small organic compounds, nucleic acids including oligonucleotides, and peptides. Small organic compounds suitably may have e.g. a molecular weight of more than about 40 or 50 yet less than about 2,500. Candidate agents may comprise functional chemical groups that interact with proteins and/or DNA.

The test compounds of the present invention can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the one-bead one-compound library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci.* U.S.A. 90:6909; Erb et al. (1994) *Proc. Natl. Acad. Sci.* USA 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Nat'l Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In another preferred embodiment, the candidate therapeutic agent comprises, proteins, peptides, organic molecules, inorganic molecules, nucleic acid molecules, and the like. These molecules can be natural, e.g. from plants, fungus, bacteria etc., or can be synthesized or synthetic.

A prototype compound may be believed to have therapeutic activity on the basis of any information available to the artisan. For example, a prototype compound may be believed to have therapeutic activity on the basis of information contained in the Physician's Desk Reference. In addition, by way of non-limiting example, a compound may be believed to have therapeutic activity on the basis of experience of a clinician, structure of the compound, structural activity relationship data, $EC_{50}$, assay data, $IC_{50}$ assay data, animal or clinical studies, or any other basis, or combination of such bases.

A therapeutically-active compound is a compound that has therapeutic activity, including for example, the ability of a compound to induce a specified response when administered to a subject or tested in vitro. Therapeutic activity includes treatment of a disease or condition, including both prophylactic and ameliorative treatment. Treatment of a disease or condition can include improvement of a disease or condition by any amount, including prevention, amelioration, and elimination of the disease or condition. Therapeutic activity may be conducted against any disease or condition, including in a preferred embodiment against any disease or disorder associated with TNFα induced activation of NF-κB. In order to determine therapeutic activity any method by which therapeutic activity of a compound may be evaluated can be used. For example, both in vivo and in vitro methods can be used, including for example, clinical evaluation, $EC_{50}$, and $IC_{50}$ assays, and dose response curves.

Candidate compounds for use with an assay of the present invention or identified by assays of the present invention as useful pharmacological agents can be pharmacological agents already known in the art or variations thereof or can be compounds previously unknown to have any pharmacological activity. The candidate compounds can be naturally occurring or designed in the laboratory. Candidate compounds can comprise a single diastereomer, more than one diastereomer, or a single enantiomer, or more than one enantiomer.

Candidate compounds can be isolated, from microorganisms, animals or plants, for example, and can be produced recombinantly, or synthesized by chemical methods known in the art. If desired, candidate compounds of the present invention can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries. The other four approaches are applicable to polypeptide, non-peptide oligomer, or small molecule libraries of compounds and are preferred approaches in the present invention. See Lam, *Anticancer Drug Des.* 12:145-167 (1997).

In an embodiment, the present invention provides a method of identifying a candidate compound as a suitable prodrug. A suitable prodrug includes any prodrug that may be identified by the methods of the present invention. Any method apparent to the artisan may be used to identify a candidate compound as a suitable prodrug.

In another aspect, the present invention provides methods of screening candidate compounds for suitability as therapeutic agents. Screening for suitability of therapeutic agents may include assessment of one, some or many criteria relating to the compound that may affect the ability of the compound as a therapeutic agent. Factors such as, for example, efficacy, safety, efficiency, retention, localization, tissue selectivity, degradation, or intracellular persistence may be considered. In one embodiment, a method of screening candidate compounds for suitability as therapeutic agents comprises providing a candidate compound identified as a suitable prodrug, determining the therapeutic activity of the candidate compound, and determining the intracellular persistence of the candidate compound. Intracellular persistence can be measured by any technique apparent to the skilled artisan, such as for example by radioactive tracer, heavy isotope labeling, or LCMS.

In screening compounds for suitability as therapeutic agents, intracellular persistence of the candidate compound is evaluated. In a preferred embodiment, the agents are evaluated for their ability to modulate NF-κB and this evaluation may comprise, for example, evaluation of NF-κB activation by TNFα and/or inhibition of TNFα over a period of time in response to a candidate therapeutic agent. In a preferred embodiment, activation of NF-κB in the presence or absence of the candidate therapeutic compound in human tissue is determined. Any technique known to the art worker for determining NF-κB activation, or induction of other markers may be used in the present invention. Some examples are the response to and induction of IL-2, the induction of TAP1 and MHC molecules by NF-kB, and many aspects of the inflammatory response, e.g. induction of IL-1 (alpha and beta), TNF-alpha and leukocyte adhesion molecules (E-selectin, VCAM-1 and ICAM-1). Moreover, NF-kB is involved in many aspects of cell growth, differentiation and proliferation via the induction of certain growth and transcription factors (e.g. c-myc, ras and p53). See, also, the experimental details in the examples section which follows.

A further aspect of the present invention relates to methods of inhibiting the activity of a condition or disease associated with TNFα induced activation of NF-κB comprising the step of treating a sample or subject believed to have a disease or condition with a prodrug identified by a compound of the invention. Compositions of the invention act as identifiers for prodrugs that have therapeutic activity against a disease or condition. In a preferred aspect, compositions of the invention act as identifiers for drugs that show therapeutic activity against conditions including for example conditions associated with inflammatory diseases or disorders.

In another preferred embodiment, soluble and/or membrane-bound forms of isolated proteins, mutants or biologically active portions thereof, can be used in the assays if desired. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON™ X-100, TRITON™ X-114, THESIT™, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

Cell-free assays can also be used for identifying drugs or agents that inhibit the activity of a condition or disease associated with TNFα induced activation of NF-κB and this involves preparing a reaction mixture which includes MCP-1, CXCL-1, MIP-2, RANTES, ICAM-1, iNOS, VCAM-1, NF-κB, or TNFα molecules, and the test compound under conditions and time periods to allow the measurement of the molecules' activity over time, etc, over a range of values and concentrations of test agents.

The enzymatic activity can be also be detected, e.g., using fluorescence energy transfer (FET) (see, for example, Lakowicz et al., U.S. Pat. No. 5,631,169; Stavrianopoulos, et al, U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorometric detection means well known in the art (e.g., using a fluorimeter).

In another embodiment, determining the ability of for example, TNFα to bind or "dock" to a target molecule which can induce NF-κB activation, can be accomplished using real-time Biomolecular Interaction Analysis (BIA) (see, e.g., Sjolander, S, and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BLAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target product or the test substance is anchored onto a solid phase. The target product/test compound complexes anchored on the solid phase can be detected at the end of the reaction. Preferably, the target product can be anchored onto a solid surface, and the test compound, (which is not anchored), can be labeled, either directly or indirectly, with detectable labels discussed herein.

Candidate agents may be obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of e.g. bacterial, fungal and animal extracts are available or readily produced.

Chemical Libraries:

Developments in combinatorial chemistry allow the rapid and economical synthesis of hundreds to thousands of discrete compounds. These compounds are typically arrayed in moderate-sized libraries of small molecules designed for efficient screening. Combinatorial methods can be used to generate unbiased libraries suitable for the identification of novel compounds. In addition, smaller, less diverse libraries can be generated that are descended from a single parent compound with a previously determined biological activity. In either case, the lack of efficient screening systems to specifically target therapeutically relevant biological molecules produced by combinatorial chemistry such as inhibitors of important enzymes hampers the optimal use of these resources.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in a large number of combinations, and potentially in every possible way, for a given compound length (i.e., the number of amino acids in a polypeptide compound). Millions of chemical compounds can be synthesized through such combinatorial mixing of chemical building blocks.

A "library" may comprise from 2 to 50,000,000 diverse member compounds. Preferably, a library comprises at least 48 diverse compounds, preferably 96 or more diverse compounds, more preferably 384 or more diverse compounds, more preferably, 10,000 or more diverse compounds, preferably more than 100,000 diverse members and most preferably more than 1,000,000 diverse member compounds. By "diverse" it is meant that greater than 50% of the compounds in a library have chemical structures that are not identical to any other member of the library. Preferably, greater than 75% of the compounds in a library have chemical structures that are not identical to any other member of the collection, more preferably greater than 90% and most preferably greater than about 99%.

The preparation of combinatorial chemical libraries is well known to those of skill in the art. For reviews, see Thompson et al., Synthesis and application of small molecule libraries, *Chem Rev* 96:555-600, 1996; Kenan et al., Exploring molecular diversity with combinatorial shape libraries, *Trends Biochem Sci* 19:57-64, 1994; Janda, Tagged versus untagged libraries: methods for the generation and screening of combinatorial chemical libraries, *Proc Natl Acad Sci* USA. 91:10779-85, 1994; Lebl et al., One-bead-one-structure combinatorial libraries, *Biopolymers* 37:177-98, 1995; Eichler et al., Peptide, peptidomimetic, and organic synthetic combinatorial libraries, *Med Res Rev.* 15:481-96, 1995; Chabala, Solid-phase combinatorial chemistry and novel tagging methods for identifying leads, *Curr Opin Biotechnol.* 6:632-9, 1995; Dolle, Discovery of enzyme inhibitors through combinatorial chemistry, *Mol Divers.* 2:223-36, 1997; Fauchere et al., Peptide and nonpeptide lead discovery using robotically synthesized soluble libraries, *Can J. Physiol Pharmacol.* 75:683-9, 1997; Eichler et al., Generation and utilization of synthetic combinatorial libraries, *Mol Med Today* 1: 174-80, 1995; and Kay et al., Identification of enzyme inhibitors from phage-displayed combinatorial peptide libraries, *Comb Chem High Throughput Screen* 4:535-43, 2001.

Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci.* USA, 90:6909-6913 (1993)); vinylogous polypeptides (Hagihara, et al., *J. Amer. Chem. Soc.* 114:6568 (1992)); nonpeptidal peptidomimetics with β-D-glucose scaffolding (Hirschmann, et al., *J. Amer. Chem. Soc.,* 114:9217-9218 (1992)); analogous organic syntheses of small compound libraries (Chen, et al., *J. Amer. Chem. Soc.,* 116:2661 (1994)); oligocarbamates (Cho, et al., *Science,* 261: 1303 (1993)); and/or peptidyl phosphonates (Campbell, et al., *J. Org. Chem.* 59:658 (1994)); nucleic acid libraries (see, Ausubel, Berger and Sambrook, all supra); peptide nucleic acid libraries (see, e.g., U.S. Pat. No. 5,539,083); antibody libraries (see, e.g., Vaughn, et al., *Nature Biotechnology,* 14(3):309-314 (1996) and PCT/US96/10287); carbohydrate libraries (see, e.g., Liang, et al., *Science,* 274:1520-1522 (1996) and U.S. Pat. No. 5,593,853); small organic molecule libraries (see, e.g., benzodiazepines, Baum C&E News, January 18, page 33 (1993); isoprenoids (U.S. Pat. No. 5,569, 588); thiazolidinones and metathiazanones (U.S. Pat. No. 5,549,974); pyrrolidines (U.S. Pat. Nos. 5,525,735 and 5,519, 134); morpholino compounds (U.S. Pat. No. 5,506,337); benzodiazepines (U.S. Pat. No. 5,288,514); and the like.

Devices for the preparation of combinatorial libraries are commercially available (see, e.g., 357 MPS, 390 MPS, Advanced Chem. Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd., Moscow, RU, 3D Pharmaceuticals, Exton, Pa., Martek Bio sciences, Columbia, Md., etc.).

Small Molecules:

Small molecule test compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, *Curr. Opin. Chem. Bio.,* 1:60 (1997). In addition, a number of small molecule libraries are commercially available.

The whole procedure can be fully automated. For example, sampling of sample materials may be accomplished with a plurality of steps, which include withdrawing a sample from a sample container and delivering at least a portion of the withdrawn sample to test platform. Sampling may also include additional steps, particularly and preferably, sample preparation steps. In one approach, only one sample is withdrawn into the auto-sampler probe at a time and only one sample resides in the probe at one time. In other embodiments, multiple samples may be drawn into the auto-sampler probe separated by solvents. In still other embodiments, multiple probes may be used in parallel for auto sampling.

In the general case, sampling can be effected manually, in a semi-automatic manner or in an automatic manner. A sample can be withdrawn from a sample container manually, for example, with a pipette or with a syringe-type manual probe, and then manually delivered to a loading port or an injection port of a characterization system. In a semi-automatic protocol, some aspect of the protocol is effected automatically (e.g., delivery), but some other aspect requires manual intervention (e.g., withdrawal of samples from a process control line). Preferably, however, the sample(s) are withdrawn from a sample container and delivered to the characterization system, in a fully automated manner—for example, with an auto-sampler.

In one embodiment, auto-sampling may be done using a microprocessor controlling an automated system (e.g., a robot arm). Preferably, the microprocessor is user-programmable to accommodate libraries of samples having varying arrangements of samples (e.g., square arrays with "n-rows" by "n-columns," rectangular arrays with "n-rows" by "m-columns," round arrays, triangular arrays with "r-" by "r-" by "r-" equilateral sides, triangular arrays with "r-base" by "s-" by "s-" isosceles sides, etc., where n, m, r, and s are integers).

Automated sampling of sample materials optionally may be effected with an auto-sampler having a heated injection probe (tip). An example of one such auto sampler is disclosed in U.S. Pat. No. 6,175,409 B1 (incorporated by reference).

According to the present invention, one or more systems, methods or both are used to identify a plurality of sample materials. Though manual or semi-automated systems and methods are possible, preferably an automated system or method is employed. A variety of robotic or automatic systems are available for automatically or programmably providing predetermined motions for handling, contacting, dispensing, or otherwise manipulating materials in solid, fluid liquid or gas form according to a predetermined protocol. Such systems may be adapted or augmented to include a variety of hardware, software or both to assist the systems in determining mechanical properties of materials. Hardware and software for augmenting the robotic systems may include, but are not limited to, sensors, transducers, data acquisition and manipulation hardware, data acquisition and manipulation software and the like. Exemplary robotic systems are commercially available from CAVRO Scientific Instruments (e.g., Model NO. RSP9652) or BioDot (Microdrop Model 3000).

Generally, the automated system includes a suitable protocol design and execution software that can be programmed with information such as synthesis, composition, location information or other information related to a library of materials positioned with respect to a substrate. The protocol design and execution software is typically in communication with robot control software for controlling a robot or other automated apparatus or system. The protocol design and execution software is also in communication with data acquisition hardware/software for collecting data from response measuring hardware. Once the data is collected in the database, analytical software may be used to analyze the data, and more specifically, to determine properties of the candidate drugs, or the data may be analyzed manually.

Data and Analysis:

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, for example Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention relates to embodiments that include methods for providing genetic information over networks such as the Internet.

Administration of Compositions to Patients

The therapeutic compositions or agents identified by the methods described herein may be administered to animals including human beings in any suitable oral formulation. For example, the compositions may be formulated in pharmaceutically acceptable carriers or diluents such as physiological saline or a buffered salt solution. Suitable carriers and diluents can be selected on the basis of standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

Dosage, toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays, measurement of cytokine levels, proteinuria and the like.

As defined herein, a therapeutically effective amount of a compound (i.e., an effective dosage) means an amount sufficient to produce a therapeutically (e.g., clinically) desirable result. The compositions can be administered one from one or more times per day to one or more times per week; including once every other day. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compounds of the invention can include a single treatment or a series of treatments.

Formulations

While it is possible for a composition to be administered alone, it is preferable to present it as a pharmaceutical formulation. The formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

The pharmaceutical formulations are preferably formulated for oral administration (solid or liquid).

The compositions may be administered to animals including human beings in any suitable formulation. Other substances may be added to the compositions to stabilize and/or preserve the compositions.

Extended Release Systems:

A first extended release system includes matrix systems, in which the agent is embedded or dispersed in a matrix of another material that serves to retard the release of the agent into an aqueous environment (i.e., the luminal fluid of the GI tract). When the agent is dispersed in a matrix of this sort, release of the drug takes place principally from the surface of the matrix. Thus the drug is released from the surface of a device, which incorporates the matrix after it diffuses through the matrix or when the surface of the device erodes, exposing the drug. In some embodiments, both mechanisms can operate simultaneously. The matrix systems may be large, i.e., tablet sized (about 1 cm), or small (<0.3 cm). The system may be unitary (e.g., a bolus), may be divided by virtue of being composed of several sub-units (for example, several capsules which constitute a single dose) which are administered substantially simultaneously, or may comprise a plurality of particles, also denoted a multiparticulate. A multiparticulate can have numerous formulation applications. For example, a multiparticulate may be used as a powder for filling a capsule shell, or used per se for mixing with food to ease the intake.

In a specific embodiment, a matrix multiparticulate, comprises a plurality of the agent-containing particles, each particle comprising the agent and/or an analogue thereof e.g. in the form of a solid solution/dispersion with one or more excipients selected to form a matrix capable of controlling the dissolution rate of the agent into an aqueous medium. The matrix materials useful for this embodiment are generally hydrophobic materials such as waxes, some cellulose derivatives, or other hydrophobic polymers. If needed, the matrix materials may optionally be formulated with hydrophobic materials, which can be used as binders or as enhancers. Matrix materials useful for the manufacture of these dosage forms such as: ethylcellulose, waxes such as paraffin, modified vegetable oils, carnauba wax, hydrogenated castor oil, beeswax, and the like, as well as synthetic polymers such as poly(vinyl chloride), poly(vinyl acetate), copolymers of vinyl acetate and ethylene, polystyrene, and the like. Water soluble or hydrophilic binders or release modifying agents which can optionally be formulated into the matrix include hydrophilic polymers such as hydroxypropyl cellulose (HPC), hydroxypropyl methyl cellulose (HPMC), methyl cellulose, poly(N-vinyl-2-pyrrolidinone) (PVP), poly(ethylene oxide) (PEO), poly(vinyl alcohol) (PVA), xanthan gum, carrageenan, and other such natural and synthetic materials. In addition, materials, which function as release-modifying agents include water-soluble materials such as sugars or salts. Preferred water-soluble materials include lactose, sucrose, glucose, and mannitol, as well as hydrophilic polymers like e.g. HPC, HPMC, and PVP.

In a specific embodiment, a multiparticulate product is defined as being processed by controlled agglomeration. In this case the agent is dissolved or partly dissolved in a suitable meltable carrier and sprayed on carrier particles comprising the matrix substance.

Dose:

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "treatment effective amount" can vary. However, using the assay methods described herein, one skilled in the art can readily assess the potency and efficacy of a candidate compound of the presently disclosed subject matter and adjust the therapeutic regimen accordingly.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the art and are within the scope of embodiments of the present invention.

Example 1

PPS Prevents Progression of Established Atherosclerosis

Pentosan polysulfate (PPS), a heparinoid compound essentially devoid of anticoagulant activity, modulates cell growth and metalloproteinase (MMP) activity in vascular smooth muscle cells. The effect of PPS on the progression of established atherosclerosis in Watanabe heritable hypercholesterolemic rabbits (WHHL) was investigated.

Materials and Methods

Reagents:

Pentosan polysulfate (PPS; ELMIRON®) was provided by IVAX Corp. (Miami, Fla.). Tissue culture reagents were purchased from Gibco BRL (Grand Island, N.Y.). 10% gelatin polyacrylamide zymography gels were from Novex (San Diego, Calif.). The First Strand TNF synthesis kit was from Boehringer Mannheim (Indianapolis, Ind.). All other reagents were from Sigma Chemical Co. (St. Louis, Mo.).

In Vivo Study Protocol:

3-month-old female WHHL rabbits, obtained from the Institute for Experimental Animals, Kobe University School of Medicine (Shiomi M, et al., *Arterioscler Thromb* 1994; 14: 931-937), were fed a standard diet supplemented with 0.5% cholesterol for 45 days. Preliminary experiments showed that severe atherosclerotic lesions developed in this time frame. Twenty rabbits with established lesions were randomized into two groups, one (PPS group) receiving PPS (30 mg/kg BW daily) added to the drinking water, and the other (Control group) receiving tap water for the next 30 days. This dose of PPS was selected on the basis of preliminary dose-response experiments as the highest dose with no effect on blood coagulation. Hemoglobin levels remained unchanged and the feces remained guaiac negative throughout the study. After 30 days, the rabbits were anesthetized with ketamine hydrochloride and xylazine (60 mg and 6 mg/kg BW, respectively), and exsanguinated. Five from each group were perfusion-fixed with 4% phosphate-buffered formaldehyde solution through the femoral vein. The remaining 10 rabbits were anesthetized and perfused with saline, and aortic ring sections were snap-frozen in liquid nitrogen for analysis by zymography and reverse-zymography. Aortas were also removed from an additional 5 untreated 4.5 month-old WHHL rabbits which had been fed the high-cholesterol diet for 1.5 months, to serve as controls.

All animal care and procedures were in accordance with the guidelines of the American Association for Accreditation for Laboratory Animal Care and the National Institutes of Health.

Plasma Lipid and Lipoprotein Analyses:

Blood was drawn from rabbits after a 12-hour fast into tubes containing EDTA at the beginning of the study, every two weeks during treatment with the atherogenic diet, and at the end of the study. The total cholesterol and triglyceride concentrations (Sigma) as well as unesterified cholesterol and phospholipids (Wako Chemicals, Richmond, Va.) were determined on plasma samples using enzymatic methods on a Hitachi 911 Autoanalyzer (Boehringer Mannheim). Post-heparin hepatic lipase activity was determined as described (Iverius P H, Brunzell J D. *Am J Physiol* 1985; 249: E107-E114).

Morphologic Analysis:

The degree of aortic atherosclerosis was evaluated by measuring the percent lesion area on the surface of the whole intimal (surface area of lesion/surface area of the whole intima) in the region between the aortic arch and the emergence of the renal arteries. Moreover, serial cross-sectional tissue samples (≈3 mm in length) taken from the aortic arch to the ileal bifurcation were post-fixed in paraformaldehyde (4% wt/vol.) and processed for histological analysis. The specimens were then embedded in paraffin, and 4-μm-thick sections were stained with hematoxylin and eosin (H&E). The ratio of intima to media (I/M ratio) was measured by computer-aided morphometric analysis in three consecutive cross-sectional sections of the aortic arch and the abdominal aorta, near the origin of the renal arteries, as described (Shindo J, et al., *Circulation* 1999; 99: 2150-2156). To avoid errors due to the heterogeneity of atherosclerotic lesions, the cross sections containing the thickest atherosclerotic lesions were selected individually from the aortic arch and used for the analysis of the cross-sectional areas of atherosclerotic lesions (Shindo J, et al., *Circulation* 1999; 99: 2150-2156). Percentage of the area occupied by macrophages and collagen were measured by computer-aided morphometric analysis on aortic cross sections stained immunohistochemically with RAM-11 antibody (DAKO Corp.) or Sirius red, respectively.

Cell Preparation and Experimental Conditions:

Human pro-monocytic U937 cells were obtained from American Type Culture Collection (Manassas, Va.) and grown in RPMI medium supplemented with 10% FBS. U937 cells were plated in six-well plates at a density of $5 \times 10^6$ cells/ml. The cells were then stimulated with 10 ng/ml TNF-α, in the presence or absence of either increasing concentrations of PPS (10-100 μg/ml) or heparin (100 μg/ml), and incubated at 37° C. for 3 hours. Following stimulation, cells were placed in 0.1% BSA-serum-free medium for 16-18 hours. The media was then collected, centrifuged, and supernatants were stored at −80° C. for the assessment of MMP activity. The cell number was determined by direct cell counting.

Human peripheral blood monocytes were isolated as previously described (Valone F H, Epstein L B. *J Immunol*. 1988; 141: 3945-3950), and maintained in medium 199 supplemented with 2% human serum for in vitro differentiation into macrophages (Camussi G, et al., *J Exp Med*. 1987; 166: 1390-1404).

Zymography and Reverse Zymography:

MMP activity in aortic extracts and conditioned media from monocytes was assessed, as previously described (Jacot T A, et al., *Lab Invest*. 1996; 75:791-79). Briefly, aortic segments were homogenized and extracted in RIPA buffer (25 mM Tris, pH 7.4, 150 mM KCl, 5 mM EDTA, 1% Nonidet P-40, 0.5% sodium deoxycholate, and 0.1% SDS). Insoluble material was precipitated by centrifugation, and soluble extracts were collected and stored at −20° C. for further analysis. For in vitro experiments, cell supernatants were centrifuged to remove cellular debris, and diluted appropriately to normalize for cell number. Aortic extracts and conditioned media were then mixed with sample buffer (1% SDS, 0.08 M Tris pH 6.8, 4% glycerol, and 0.006% bromophenol blue), and loaded onto a 10% gelatin polyacrylamide gel, and processed as described (Jacot T A, et al., *Lab Invest*. 1996; 75:791-79). For reverse zymography, samples were loaded onto a 15% gelatin polyacrylamide gel containing 0.5% porcine gelatin and 6 μg recombinant gelatinase A, and processed as described (Elliot S J, et al., *J Am Soc Nephrol*. 1999; 10: 62-68).

Evaluation of Net MMP Activity:

MMP-2/MMP-9 net activity in aortic extracts was evaluated by using a synthetic colorimetric substrate [Ac-Pro-Leu-Gly-(2-mercapto-4-methylpentanoyl)-Leu-Gly-Oet; Calbiochem, Cambridge, Mass.], according to the manufacturer's directions.

Statistical Analysis:

Data are presented as mean±SEM. Differences among multiple groups were analyzed by one-way analysis of variance (ANOVA) in combination with Bonferroni's multiple comparison test. Lipid levels were expressed as percent of the basal values for each individual animal and analyzed by using repeated measures ANOVA. Where appropriate, statistical differences were assessed using Student's t test (Prism, GraphPad 3.02, San Diego, Calif.). A p value of <0.05 was considered significant.

Results

Figures 2A, 2B, 2C:
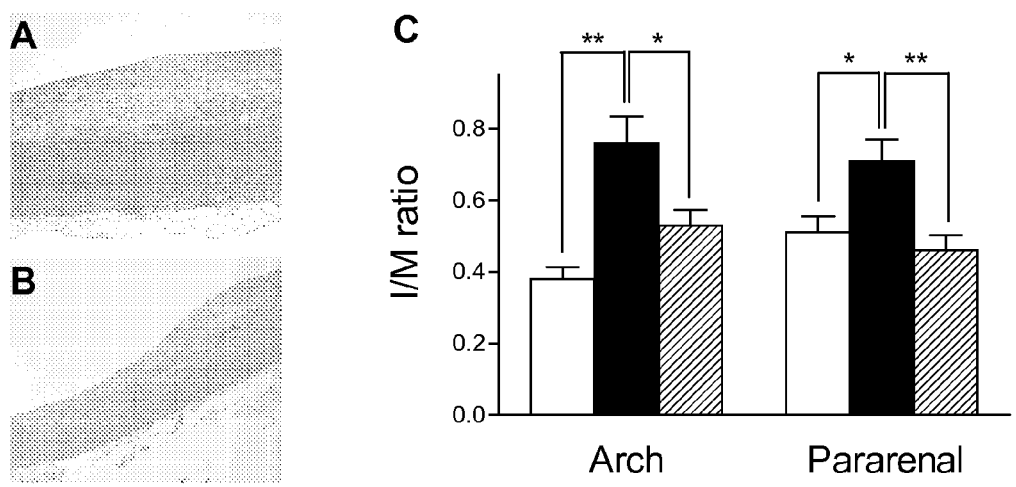
FIGS. 2A-2C show representative micrographs of cross sections of aortic arch from WHHL rabbits fed a HC-diet 75 days.

Effect of PPS on the Progression of Established Atherosclerotic Lesions in WHHL Rabbits:

The progression of established atherosclerosis, induced by diet in WHHL rabbits was markedly decreased by PPS treatment (FIGS. 1A-1C). The differences between treated and control groups were evident by gross examination. The origins of arteries in the water-treated controls were engulfed by large plaques and the aortic surface was irregular due to the presence of multiple plaques of varying size. The aortic wall was thickened and it was less pliable in the water-treated group than in the PPS-treated group. The aortic surface in the PPS-treated group was relatively smooth and glistening and the plaques in this group had a smooth flattened contour and were most prominent around the origins of arteries. Analysis of the intimal surface showed that the percent surface area of the intima occupied by lesions in the PPS-treated group was reduced by approximately one-third compared to the water-treated controls (FIG. 1C). Microscopic examination of the aorta in the PPS-treated group showed that the plaques were thinner and contained few foam cells, no increase in the number of the cells in the intima or media, and a reduction in the intima/media ratio (FIGS. 2A, 2B). Atherosclerotic lesions were quantified on H&E-stained sections by measuring intima and media by computer-aided morphometric analysis at the aortic arch and in the abdominal aorta, close to the emergence of the renal arteries. The calculated intima/media ratio (I/M) in both regions was found to be significantly increased from 45 to 75 days in WHHL rabbits fed an HC-diet (FIG. 2C, black bars). In contrast, the PM ratio in PPS-treated animals was significantly lower after 75 days of HC-diet (FIG. 2C, hatched bars), compared to water-treated controls. The FM ratio in the animals fed a HC-diet for 45 days and treated with oral PPS for an additional 30 days was not significantly different from that measured in WHHL rabbits fed a HC-diet for 45 days (FIG. 2C, white bars). There was a trend towards a reversion of the aortic lesions in the pararenal region of the PPS-treated animals (FIG. 2C, white bars).

Microscopic examination revealed that the plaques in the PPS-treated group were covered by an organized fibrous cap and had fewer macrophages, whereas the plaques in the water-treated group lacked a fibrous cap and contained a dense infiltrate of macrophages. The ratio of area of the plaque containing macrophages to total plaque area was evaluated to determine whether PPS had an effect on macrophage recruitment into the plaque. The area containing macrophages, relative to the total plaque area, was decreased in PPS-treated rabbits (35.56±1.51%) versus untreated controls (51.86±5.99%, P<0.05, FIGS. 3A-3C). Collagen deposition within the atheroma was evaluated using aortic arch tissue sections stained with Sirius red from both control and PPS-treated rabbits. There was significantly more Sirius red staining in plaques of PPS-treated rabbits (47.43±2.93%) versus controls (31.39±2.87%, P<0.01, FIGS. 3D-3F).

Effect of PPS on Plasma Lipids in WHHL Rabbits:

WHHL rabbits on the atherogenic diet had substantially increased plasma total (240.42±18.22%) and free (377.23±62.11%) cholesterol, as well as phospholipid (221.30±33.27%) concentrations, while triglyceride concentrations decreased (36.44±9.49%) at 45 days (Table 1). The levels in PPS-treated animals were not significantly different after 75 days of HC-diet than at 45 days, although a trend towards a reduction of lipid levels after PPS treatment was observed (Table 1). The activity of post-heparin hepatic lipase, determined at the end of treatment period, revealed no differences between PPS- and water-treated (control) WHHL rabbits.

TABLE 1

Plasma Lipid Concentrations.

| | Baseline | 45 days HC-diet | 75 days HC-diet |
|---|---|---|---|
| Total cholesterol (mg/dl) | | | |
| Control (water-treated) | 845.57 ± 67.50 | 1979.28 ± 77.75 | 1894.34 ± 57.38 |
| PPS-treated | 901.18 ± 50.30 | 2133.28 ± 85.04 | 1565.40 ± 212.07 |
| Free cholesterol mg/dl | | | |
| Control (water-treated) | 250.68 ± 22.04 | 962.95 ± 127.22 | 967.16 ± 93.41 |
| PPS-treated | 282.92 ± 13.03 | 1038.52 ± 128.80 | 785.46 ± 93.22 |
| Triglycerides (mg/dl) | | | |
| Control (water-treated) | 749.58 ± 119.84 | 237.81 ± 60.50 | 274.76 ± 69.29 |
| PPS-treated | 762.91 ± 72.13 | 331.28 ± 86.61 | 184.10 ± 30.19 |
| Phospholipids (mg/dl) | | | |
| Control (water-treated) | 503.59 ± 41.63 | 1118.03 ± 129.80 | 1069.83 ± 102.28 |
| PPS-treated | 574.59 ± 26.44 | 1241.09 ± 142.75 | 878.17 ± 107.98 |

Legend for Table 1: Plasma lipid levels were measured at baseline (3-months of age) and after 45 and 75 days on a high-cholesterol (HC)-diet. After 45 days on a HC-diet, WHHL rabbits were randomized to receive PPS (30 μg/kg BW daily) added to the drinking water or just tap water (Control) for the next 30 days, as detailed in the Materials and Methods section. Data are expressed as mg/dl, mean ± SEM of 5 animals in each group.

Figure 4A:
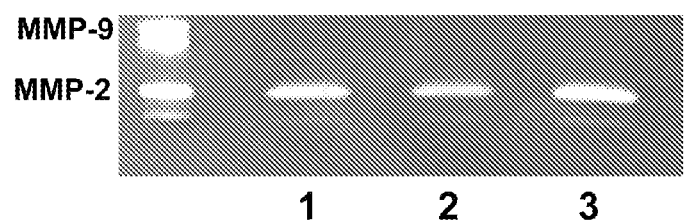
FIGS. 4A-4B show MMP activity in aortic extracts from WHHL rabbits.
Figure 4B:
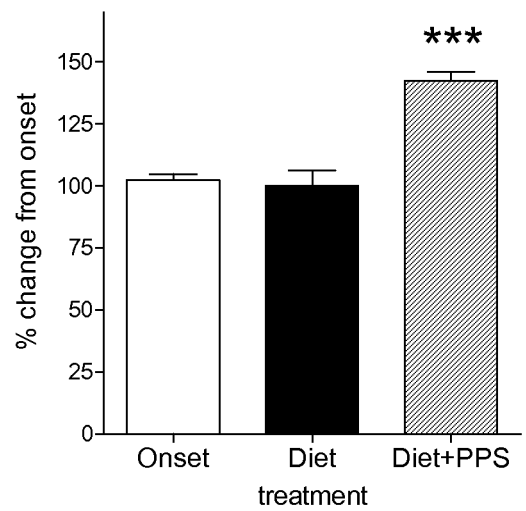

Effect of PPS on Ex Vivo MMP and TIMP Activities in Aortic Extracts:

MMP activity was assessed in extracts of cross-sections aortic arch region by using a synthetic colorimetric substrate and by zymography. Net MMP-2/MMP-9 activity was reduced in WHHL rabbits treated with PPS compared to water-treated animals by 27.74±4.32% (P<0.05). On the other hand, MMP-2 activity was significantly increased in aortic extracts obtained from PPS-treated WHHL rabbits (FIGS. 4A, 4B).

Figure 5A:
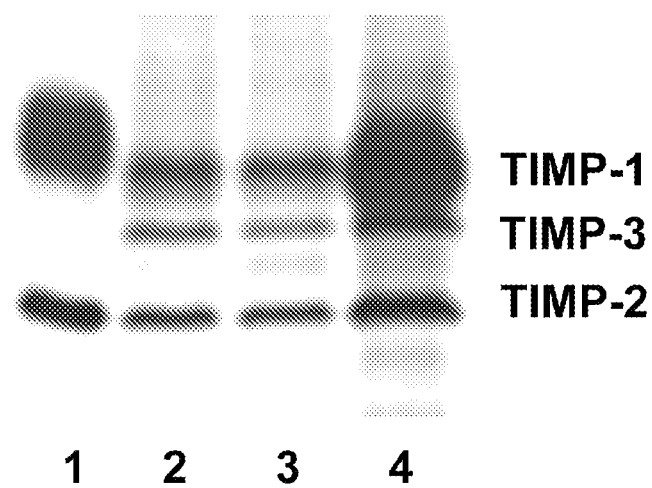
FIGS. 5A-5B show TIMP activity in aortic extracts from WHHL rabbits.
Figure 5B:
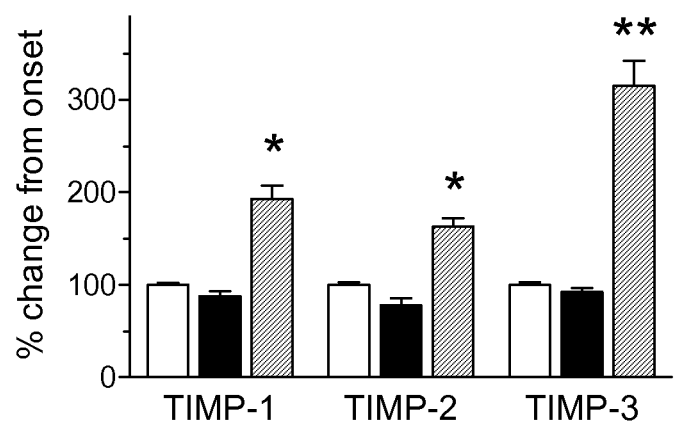

The activities of TIMPs, specific endogenous inhibitors of MMPs, were evaluated by reverse-zymography. TIMP-1, -2, and -3 activities were increased after 45 days on the atherogenic diet (FIGS. 5A, 5B). Treatment with PPS induced a marked increase in the activity of TIMP-1, -2, and -3 (FIG. 5A, lane 4).

In Vitro PPS Effect on MMP and TIMP Activities by Monocytic Cells:

Without wishing to be bound by theory, increased MMP activity in monocyte-macrophages may correlate with the development of acute complications such as plaque rupture and thrombosis. As such, the effects of PPS on MMP activity in U937 cells and human peripheral blood-derived macrophages from normal subjects were evaluated.

Figures 6A, 6B, 6C, 6D, 6E, 6F:
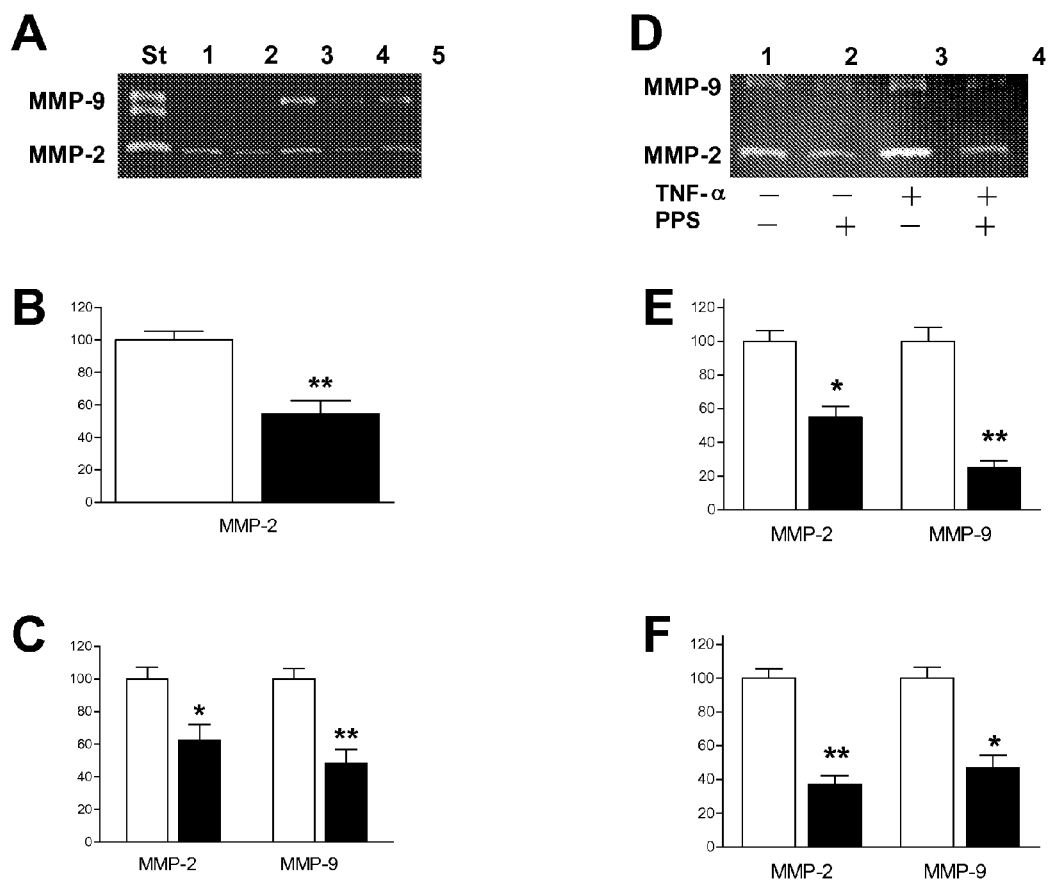
FIGS. 6A-6F show MMP activity in human pro-monocytic U937 cells and human peripheral blood-derived macrophages.

Unstimulated U937 cells expressed only MMP-2 activity. However, after the addition of TNF-α; they expressed both MMP-2 and MMP-9 activities which is characteristic of the in vitro macrophage phenotype (Welgus H G, et al. *J Clin Invest.* 1990; 86: 1496-1502). PPS treatment decreased MMP-2 activity (45.40%±9.68%)(P<0.01) in unstimulated U937 cells (FIGS. 6A and 6B). This was comparable to the effect observed following heparin treatment (FIG. 6A, lane 5). PPS treatment reduced both MMP-2 (37.73%±12.17%; P<0.05) and MMP-9 (51.70%±10.77%; P<0.01) activity in U937 cells stimulated with 10 ng/ml TNF-α (FIGS. 6A and 6C). Dose-response experiments showed that the PPS effect was evident at 25 μg/ml and maximal at 75-100 μg/ml.

PPS also had an inhibitory effect on MMP production by TNF-α stimulated human peripheral blood-derived macrophages (FIGS. 6D-6F). PPS had no effect on cell viability, as assessed by trypan blue staining.

Discussion

The present study shows that oral treatment with PPS prevents the progression of established atherosclerotic lesions in aortas of WHHL rabbits fed a high-fat diet. This effect was not related to the anticoagulant activity of PPS, because it is essentially devoid of anticoagulant activity ($1/15^{th}$ of that of heparin), and bleeding was not observed. The reduction of atherosclerotic lesions detected in the animals treated with PPS did not appear to be related to a change in the plasma levels of lipids, since total and free cholesterol, triglyceride and phospholipid concentrations did not significantly differ between the PPS-treated and the control groups. In addition, no difference in the activity of post-heparin hepatic lipase was detected.

Heparin and heparin-like molecules have not been commonly employed as a treatment for chronic progressive diseases such as atherosclerosis have not been commonly used because they must be administered parenterally. This limitation does not apply to PPS, since it can be given orally. PPS prevents the development of glomerular and tubulointerstitial fibrosis in streptozotocin-induced diabetes, bGH transgenic mice, and rats with cyclosporin A nephropathy or 5/6 nephrectomy. In addition, PPS reduces the symptoms of inflammatory arthritis and to decrease infarct size in an experimental myocardial ischemia/reperfusion injury model (Tahhehco E J, et al. *J Cardiovasc Pharmacol* 1999; 34: 153-161).

It was found herein, that atherosclerotic plaques in PPS-treated WHHL rabbits contained fewer macrophages than those in water-treated controls. PPS and heparin may modulate the inflammatory response by inhibiting the activation of the complement cascade (Kilgore K S, et al. *J Pharmacol Exp Ther* 1998; 285: 987-994), binding or displacing inflammatory cytokines (Tanaka Y, et al. *Immunol Today* 1993; 14: 111-114; Lotz M, et al. *J Urol* 1994; 152: 869-873), reducing nuclear factor κB activation (Sadhukhan P C, et al. *J Urol* 2002; 168: 289-292), acting as a free-radical scavenger, or reducing neutrophil adhesion and infiltration (Shah P K, et al. *Circulation*. 1995; 92: 1565-1569). Each of these mechanisms can contribute directly to reduce macrophage recruitment and improve overall plaque development and stability.

It was also found that PPS treatment increased collagen content within the atherosclerotic plaques. PPS has a role in modulating cell proliferation, as well as the synthesis and accumulation of extracellular matrix, this study focused both ex vivo and in vitro on MMP and TIMP activities. Net MMP-2/MMP-9 activity in aortic extracts of PPS-treated animals was significantly decreased. Moreover, MMP-2 activity and TIMPs were significantly more elevated in the aortic wall of PPS-treated animals. Taken together, these results suggest that the increase in TIMP activity induced by PPS treatment is quantitatively more important that the associated increase in MMP-2 activity observed in aortic extracts. The action of MMPs and TIMPs has emerged as an important determinant of the natural history of the atherosclerotic process, and of the general vascular response to injury. Increased MMP activity has been demonstrated in macrophages and smooth muscle cells in the rupture-prone shoulder region of atherosclerotic plaques, in human-monocyte-derived macrophages and in foam cells derived from the aortas of cholesterol-fed rabbits, leading to the hypothesis that increased MMP activity may directly cause plaque instability and rupture, although studies questioning this conclusion have also been reported. The therapeutic efficacy of many compounds which inhibit MMP activity, including TGF-β, corticosteroids, heparin and several synthetic MMP inhibitors, has been tested in different animal models of vascular damage, without conclusive results. It is shown herein, that reduced progression of atherosclerotic lesions in the aortas of PPS-treated WHHL rabbits is associated with decreased net collagenolytic activity and increased MMP-2 and TIMPs within the aortic wall. These effects are consistent with the conclusion that increased collagen deposition contributes to a reduction in the progression of aortic lesions.

The effect of PPS on MMP activity in monocyte/macrophages in vitro was also studied herein, and it was observed that PPS inhibited both MMP-2 and MMP-9 enzymatic activities in two types of human monocytes, a pro-monocytic cell line (U937 cells) and those derived from the peripheral blood of normal volunteers. Thus, the action of PPS may have several independent beneficial effects on established atherosclerotic lesions. One outcome could be to stabilize the amount of collagen in plaques by modulating MMP and TIMP activities within the wall of the atherosclerotic aorta. The second appears to be the reduction of macrophage infiltration within the atherosclerotic plaque. The third may be to inhibit MMP activity in monocytes/macrophages, thereby stabilizing atherosclerotic plaques, which would have the effect of reducing acute complications.

Together with the effects on the inflammatory response and on extracellular matrix deposition, other biological activities of PPS may be relevant to the progression of established atherosclerosis. PPS reduces the binding of acetylated low-density lipoproteins to endothelial cells, and selectively inactivates several heparin-binding growth factors. Furthermore, PPS is a hydrophilic molecule that carries a negative charge, two properties that promote its localization to the endothelial cell surface, preserving the integrity of the glycocalyx "shield".

In summary, it was shown herein, that the oral administration of PPS treatment retards the progression of established atherosclerosis in WHHL rabbits, effecting plasma lipid levels and post-heparin hepatic lipase activity. The PPS effect appeared to be related to its ability to reduce macrophage infiltration and to regulate MMP and TIMP activities within the wall of the atherosclerotic aorta in a manner which favors collagen deposition, rather than collagen degradation. PPS treatment increased indeed MMP-2 and TIMP activity in smooth muscle cells, while it inhibited MMP-2 and MMP-9 activities in monocytes/macrophages.

Example 2

Induction of Diabetes in Aged C57B6 Mice Results in Severe Nephropathy: Contribution of Oxidative Stress, ER Stress, and Inflammation Materials and Methods Animals:

4 and 16-17 month-old female C57B6 mice were obtained from National Institute on Aging and were injected with streptozotocin to induce diabetes. Mice were given 50 µg/g of streptozotocin in every three days, for a total of 5-8 injections. A total of 250-400 µg/g of streptozotocin was sufficient in most of mice to induce stable hyperglycemia (≥250 mg/dL). The streptozotocin dose required to establish stable diabetes was similar between 1-17 month-old and 4 month-old mice. There was less than 10% of mortality in both age groups of diabetic mice with this streptozotocin protocol. Dead mice were excluded from further study. Mice with stable diabetes at 5 or 18 months of age were selected for randomization. Female C57B6 mice were chosen as the onset and nature of renal lesions in aging was documented by the inventors herein These mice have irregular, lengthened estrous cycles around 10 to 14 months of age and the cycles usually cease at 18 months of age. 13 18 month-old diabetic mice were randomly divided into PPS treated (n=10, PPS 25 mg/kg/day in drinking water) and control (n=11) groups. No PPS treatment was given to 5 month-old diabetic mice. Both age groups of diabetic mice were followed for 4 months without insulin treatment. Body weight and blood glucose levels were monitored weekly. Urine albumin excretion was measured bi-weekly using an ELISA kit (Bethyl Laboratory Inc, Houston, Tex., USA), as previously described (Zheng F, et al. *Am J Pathol* 2003, 162:1339-1348). Urine creatinine levels were measured in the same samples and the urine albumin excretion rate was expressed as the ratio of albumin to creatinine Blood urea nitrogen (BUN) levels and serum creatinine levels were examined at sacrifice. High-performance liquid chromatography (HPLC) was applied for determining serum creatinine levels using the method described by Yuen et al. (*Am J Physiol Renal Physiol* 2004, 286:F1116-1119).

Additionally, to explore the role of ER stress in diabetic nephropathy, 5 month-old female CHOP (C/EBP homologous protein) deficient mice, obtained from the Jackson Laboratory were also made diabetic by streptozotocin (n=5). CHOP$^{-/-}$ mice with stable diabetes were followed for 4 months.

Renal Histology and Morphometry:

Mice were sacrificed 4 months after stable hyperglycemia was established. Kidneys were perfused with a saline solution and subsequently one kidney was perfusion-fixed in situ with 4% paraformaldehyde for histologic studies. The tissues were embedded in glycol methacrylate or low melting paraffin, and stained with periodic acid Schiff (PAS) and Masson's Trichrome. Tissues were also postfixed for 1 hour in 1.0% osmium tetroxide, prestained in 1.25% uranyl acetate for 1 hour, dehydrated through a series of graded alcohol solutions, and embedded in EPON epoxy resin for electron microscopy. The glomerular volume and mesangial area were determined by examining plastic embedded sections using a digitizing tablet and video camera. The relative mesangial area was expressed as mesangial/glomerular surface area. Glomerular cell number was determined by counting the nuclear number in at least 30 glomeruli of each section. The glomerular basement membrane thickness was measured by the orthogonal intercept method on electron microscopic images. To determine the number of glomerular fenestrae, the length of was fenestrated or unfenestrated glomerular capillary endothelial cytoplasm was measured. Fenestrated endothelial cell cytoplasm was generally thin whereas the thickness of the unfenestrated endothelial cell cytoplasm was twice or more increased. Tubulointerstitial lesions were scored from 0 to 4 (0, no changes; 1+, changes affecting <25% of the sample; 2+, changes affecting 25 to 50% of the sample; 3+, changes affecting 50 to 75% of the sample; 4+, changes affecting 75 to 100% of the sample) based on tubular atrophy, increase in the thickness of basement membranes and interstitial area, and clusters of inflammatory cells.

Immunohistochemistry:

Paraffin sections from non-diabetic and diabetic mice were deparaffinized prior to staining for apoptosis, makers for inflammation such as macrophages (F4/80, 1:100, Caltag Laboratories, Burlingame, Calif.) and phosphorylated NF-κB (p65 (Ser276), 1:25, Cell Signaling Technology, Inc, Danvers, Mass.), markers for oxidative stress, i.e., nitrotyrosine (1:140, Upstate Biotechnology Inc, Billerica, Mass.) and malondialdehyde (MDA, 1:100, Alpha Diagnostic International Inc, San Antonio, Tex.), and markers for endoplasmic reticulum (ER) stress, i.e., phosphorylated pancreatic ER kinase (PERK, 1:5, Santa Cruz Biotechnology, Santa Cruz, Calif.), and phosphorylated eukaryotic initiation factor 2α (eIF2α, 1:50, Stressgen Bioreagents Corp, Norwalk, Conn.).

Digital Quantitation of Immunostaining:

Stained sections were examined under light microscopy (Zeiss Axioskop, Germany). The cortical area of the kidney was digitized under ×10 objective low power with a Sony 3CCD color video camera and a meta imaging series software (Molecular Devices, Downingtown, Pa.). The area of positively stained tubules and glomeruli was measured and expressed as the percentage of total cortical area. The intensity of the staining was also assessed using the color differentiation program.

Renal Tissue Advanced Glycation End-Products (AGEs):

The amount of AGEs in kidney was determined by a competitive enzyme-linked immunosorbent assay, using monoclonal antibody reacting with N-(carboxymethyl)-lysine (4G9; Alteon, Northvale, N.J.) and values were corrected to the protein concentration in the samples. N-(carboxymethyl)-lysine-BSA was used as a standard for quantitation.

Oxyblot:

The Oxyblot protein oxidation detection kit (Chemicon International, Temecula, Calif.) was used for the measurement of overall carbonyl groups introduced into protein side chain by oxidative modification in renal tissues. 2,4-Dinitrophenylhydrazine (DNPH) derivatization was carried out for 15 minutes following the manufacturer's instruction on 10 μg of protein obtained from the kidney tissue lysate. The DNP-derivatized protein samples were separated by 12% sodium dodecyl sulfate polyacrylamide gel electrophoresis. Proteins were transferred to PVDF membranes, stained by ponceau red, and then probed with an anti-dinitrophenylhydrazine antibody. Blots were developed using a chemiluminescence detection system. No visible bands were seen in samples without reacting with DNPH prior to Western-blots.

mRNA Levels:

Total RNA was isolated from renal cortex using a PureYield RNA Midiprep kit (Promega, Madison, Wis.). The preparation was free of DNA contamination and 500 ng of total RNA from each sample was reverse-transcribed as previously described (Zheng F, Striker G E, Esposito C, Lupia E, Striker L J. *Kidney Int* 1998, 54:1999-2007; Zheng F, et al., *Am Pathol* 2003, 162:1339-1348). The levels of MCP-1 (monocyte chemoattractant protein-1), CXCL1 (c-x-c motif ligand 1), MIP2 (macrophage inflammatory protein 2), RANTES (regulated on activation, normal T cell expressed and secreted), ICAM-1 (intracellular adhesion molecule 1), GRP78 (glucose regulatory protein 78), CHOP, and IL-6 (interleukin 6) mRNA were determined by real-time polymerase chain reaction (PCR). The primers used for the measurement were:

```
MCP-1, forward,
                                        (SEQ ID NO: 1)
5'-AATTACCAGCAGCAAGTGTCC;

reverse,
                                        (SEQ ID NO: 2)
5'-GGGTCTGCACAGATCTCCTT;

RANTES, forward,
                                        (SEQ ID NO: 3)
5'-TTCCCTGTCATCGCTTGCTCT;

reverse,
                                        (SEQ ID NO: 4)
5'-CGGATGGAGATGCCGATTTT;
```

```
-continued
CXCL1, forward,
                                      (SEQ ID NO: 5)
5'-CTTGAAGGTGTTGCCCTCAG;

reverse,
                                      (SEQ ID NO: 6)
5'-AAGGGAGCTTCAGGGTCAAG;

MIP2, forward,
                                      (SEQ ID NO: 7)
5'-TCCAGAGCTTGAGTGTGACG;

reverse,
                                      (SEQ ID NO: 8)
5'-TTCAGGGTCAAGGCAAACTT;

ICAM-1, forward,
                                      (SEQ ID NO: 9)
5'-TGCTGCAGATGCTGTGAGAGT;

reverse,
                                     (SEQ ID NO: 10)
5'-AAACCCTCGACCCATGTGATC;

eNOS, forward:
                                     (SEQ ID NO: 11)
5-TAC GCA CCC AGA GCT TTT CT;

reverse:
                                     (SEQ ID NO: 12)
5-CTT GGT CAA CCG AAC GAA GT;

GRP78, forward,
                                     (SEQ ID NO: 13)
5'-TACTCGGGGCCAAATTTGAAG-3', reverse,
                                     (SEQ ID NO: 14)
5'-CATGGTAGAGCGGAACAGGT-3';

CHOP, forward,
                                     (SEQ ID NO: 15)
5'-TATCTCATCCCCAGGAAACG-3';

reverse,
                                     (SEQ ID NO: 16)
5'-GGACGCAGGGTCAAGAGTAG-3'.
``` mRNA levels were corrected by the levels of β-actin or GAPDH mRNA. The expression of TNFα mRNA in kidney was determined by both a real time and a regular PCR using the primer of forward, 5'-GCGACGTGGAACTGGCA-GAAG-3' (SEQ ID NO: 17), reverse, 5'-GGTACAAC-CCATCGGCTGGCA-3' (SEQ ID NO: 18). GAPDH and β-actin mRNA levels were measured in the same sample.

CHOP and ER Stress Induced Apoptosis in Proximal Tubular Cells:

To determine if CHOP played a role in ER stress induced renal cell death, primary proximal tubular cells were isolated from 2 month-old CHOP$^{-/-}$ and wild type mice using a method described by Sheridan et al. (*Am J Physiol* 1993, 265:F342-350). Briefly, kidneys were perfused with a phosphate buffer solution and dynabead M-450 ($5 \times 10^5$ beads/ml, Invitrogen, LA, CA). Cortices were then cut to small pieces and incubated with 0.1% collagenase and 100 u/ml DNase at 37° C. for 40 minutes. After pressing tissues through a 100 μm cell strainer (BD Biosciences, Bedford, Mass.) with a syringe plunger, glomeruli were removed by a magnetic concentrator. The remaining tissues were collected with a 40 μm cell strainer, washed and cultured with medium containing DMEM/F12 (1:1), 5 μg/ml transferrin, 5 μg/ml insulin, 50 nM hydrocortisone, 5% FBS, 100 u/ml each of penicillin and streptomycin. Cells isolated by this method were predominantly of proximal tubular origin (>90%) and were characterized by their cobblestone appearance and by positive staining for aquoporin-1 and megalin (Santa Cruz Biotechnology Inc, Santa Cruz, Calif.). Cells ($1 \times 10^4$/well in a 24-well plate) from CHOP$^{-/-}$ and wild type mice were exposed to 0.8-1.6 μg/ml of tunicamycin. 24 hours later, cells were gently washed and stained with trypan blue, the number of live cells from each well was counted.

TNFα Induced Pro-Inflammatory Genes Expression in Proximal Tubular Cells:

A proximal tubular cell line obtained from mice transgenic for SV40 T antigen was grown in DMEM containing 10% FBS. For the measurement of TNFα-stimulated gene expression, $1 \times 10^5$ proximal tubular cells were transferred to each well of a 6-well-plate. After placing the cells in 0.1% FBS medium for 24 hours, 10 ng/ml of TNFα was added to test wells. Total RNA was isolated from all wells 4 hours later. MCP-1, RANTES, CXCL1, MIP-2, ICAM-1, and iNOS mRNA levels were determined by real-time PCR as described above and corrected by β-actin mRNA levels. TNFα stimulated MCP-1 and RANTES production and release into the medium was measured in TNFα (10 ng/ml) treated and control cells at 24 hours. The amount of MCP-1 or RANTES in the medium was measured by ELISA (Invitrogen Corporation (Carlsband, Calif.).

Effect of PPS on TNFα Stimulated NE-κB Activation and Pro-Inflammatory Genes Expression in a Proximal Tubular Cell Line:

To determine the effect of PPS on TNFα induced upregulation of proinflammatory genes, proximal tubular cells were pre-treated with PPS (200 μg/ml) for 1 hour before the addition of TNFα (10 ng/ml). MCP-1, RANTES, CXCL1, MIP-2, ICAM-1, and iNOS mRNA levels were determined 4 hours later by real-time PCR. MCP-1 and RANTES production was also measured.

The activation of NF-κB and mitogen activated protein kinases including p38, JNK (Jun N-terminal kinase), and ERK (extracellular signal regulated kinase) pathways play an essential role in proinflammatory actions of TNFα. Thus, it was examined whether PPS affected the phosphorylation of IκB, ERK, p38, and JNK by TNFα. Proximal tubular cells were allowed to grow to 70% confluency in 60 mm2 petri-dish. Cell lysates were collected before or 15, 30, 60, and 120 minutes after TNFα treatment (10 ng/ml). Cells in some dishes were pre-incubated with PPS (400 μg/ml) for ½ hour before exposure to TNFα. The levels of phosphorylated IκB, ERK, p38, and JNK were determined by Western-blots. Briefly, equal amounts of protein samples (10-20 μg/lane) were loaded onto SDS-PAGE gels. After electrophoresis, proteins were transferred to nitrocellulose membranes and blotted with antibody against phosphorylated IκB, ERK, p38, or JNK (Cell signaling, Boston, Mass.). After the first analysis, the membranes were stripped to re-probe with antibody against total IκB, ERK, p38 or JNK, and ERK and finally with antibody against β-actin (Cell signaling, Boston, Mass.).

To further determine the effect of PPS on NF-κB transcription activity, proximal tubular cells were transfected with a NF-κB reporter in the presence or absence of PPS (50-200 μg/ml) and TNFα (10 ng/ml). Some cells were also transfected with a cDNA expression vector containing constitutively active IκB, dominant negative IKK, or IKK. A β-galactosidase cDNA expression vector was co-transfected with the NF-κB reporter to serve as an internal control for transfection efficiency. Luciferase and β-galactosidase activity were measured using substrate assays. The same amount of DNA (1 μg/well of 24 well plates) was used for each transfection throughout the experiments.

Additionally, NF-κB DNA binding was examined by gel mobility shift assay (EMSA). Briefly, proximal tubular cells were pre-incubated with or without PPS (800 µg/ml) for ½ hour before the addition of TNFα (10 ng/ml). Nuclear protein was extracted from cells 1 hour after treatment. A NF-κB probe was prepared by annealing complementary single-stranded oligonucleotides with 5'-ACTG overhangs (MWG Biotechnologies, Inc.) and were labeled by filling in with [-$^{32}$P]dGTP and [-$^{32}$P]dCTP using Klenow enzyme. Labeled probes were purified with Nuctrap purification columns (Roche Applied Science). EMSAs were performed using $10^5$ cpm of labeled probe and 10 µg of nuclear extracts/reaction. DNA binding complexes were separated by electrophoresis on a 5% polyacrylamide-Tris/glycine-EDTA gel, which was dried and exposed to X-ray film.

Effect of PPS on TNFα Induced Increase in Albumin Permeability in Podocytes:

$1\times10^5$ podocytes were seeded onto collagen-coated transwell filters (0.4 µM pore-size, Corning, N.Y., N.Y.) placed in the top chamber of each well of a 24-well plate. After cells reached confluence, some wells of cells were treated with TNFα (20 ng/ml), PPS (400 µg/ml), or PPS plus TNFα in 2% FBS medium for 8 hours. Then the medium from both the top and bottom chamber was completely removed, cells were washed twice with PBS and the top chamber was refilled with 0.2 ml 2% FBS medium supplemented with 0.5 mg/ml FITC-labeled BSA (Sigma Aldrich, St Louis, Mich.), while the bottom chamber was refilled with 0.6 ml 2% FBS medium supplemented with 0.5 mg/ml unlabeled BSA. At different time points, 100 µl aliquots were collected from the bottom chamber and fluorescence was measured by a fluorescence spectrophotometer (485 nm excitation, 535 nm emission). The concentration of FITC-BSA passing through the monolayer was determined by reference to a set of standard dilutions of FITC-BSA. The value of albumin flux through untreated monolayer was arbitrarily defined as 100%.

Statistical Analysis:

Values were expressed as mean±SD. ANOVA or two-tailed unpaired t test was used to evaluate the differences between the means. Significance was defined as $p<0.05$.

Results:

General:

Body weight was slightly decreased in both 9 month-old and 22 month-old diabetic mice (Table 2). There was a significant increase in heart weight to body weight ratio in 22 month-old non-diabetic mice compared to 9 month-old non-diabetic mice (Table 2). The presence of hyperglycemia for 4 months increased heart weight to body weight ratio in both 22 month-old and 9 month-old diabetic mice. There were no differences in kidney weight to body weight ratio between diabetic and non-diabetic mice. The levels of serum creatinine were relatively low in 22 month-old non-diabetic mice, being comparable to 9 month-old non-diabetic mice. The levels were significantly higher in 22 month-old diabetic mice than age matched non-diabetic mice. BUN levels were increased in 4 of 11 22 month-old diabetic mice (>35 mg/dL), but were normal in 22 month-old non-diabetic and in 9 month-old diabetic mice.

Figures 7A, 7B:
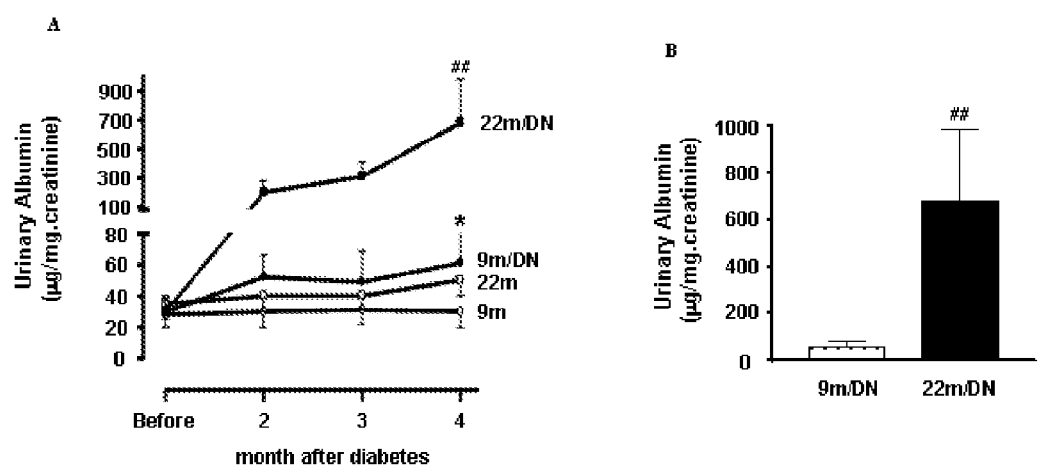
FIGS. 7A-7B show that urine albumin excretion progressively increases in 22 month-old diabetic mice.

Albuminuria:

As previously reported, young C57B6 mice were relatively resistant to diabetic nephropathy. There was a mild increase in urine albumin excretion in 9 month-old diabetic mice (albumin/creatinine ratio, diabetic, 61±25 µg/mg Cr, vs. non-diabetic, 30±10 µg/mg Cr, $p<0.05$). 22 month-old diabetic mice developed progressive albuminuria. The albumin/creatinine ratio was 200±80 µg/mg Cr after 1 month of diabetes (FIG. 7A), which was significantly higher than in age-matched 22 month-old non-diabetic (40±10 µg/mg Cr, $p<0.01$) and in 9 month-old diabetic mice ($p<0.01$). Albuminuria continued to increase in 22 month-old diabetic mice, reaching levels which were 11-fold higher than in 9 month-old diabetic mice at 4 months after diabetes onset (FIG. 7B).

Figures 8A, 8B, 8C, 8D, 8E, 8F:
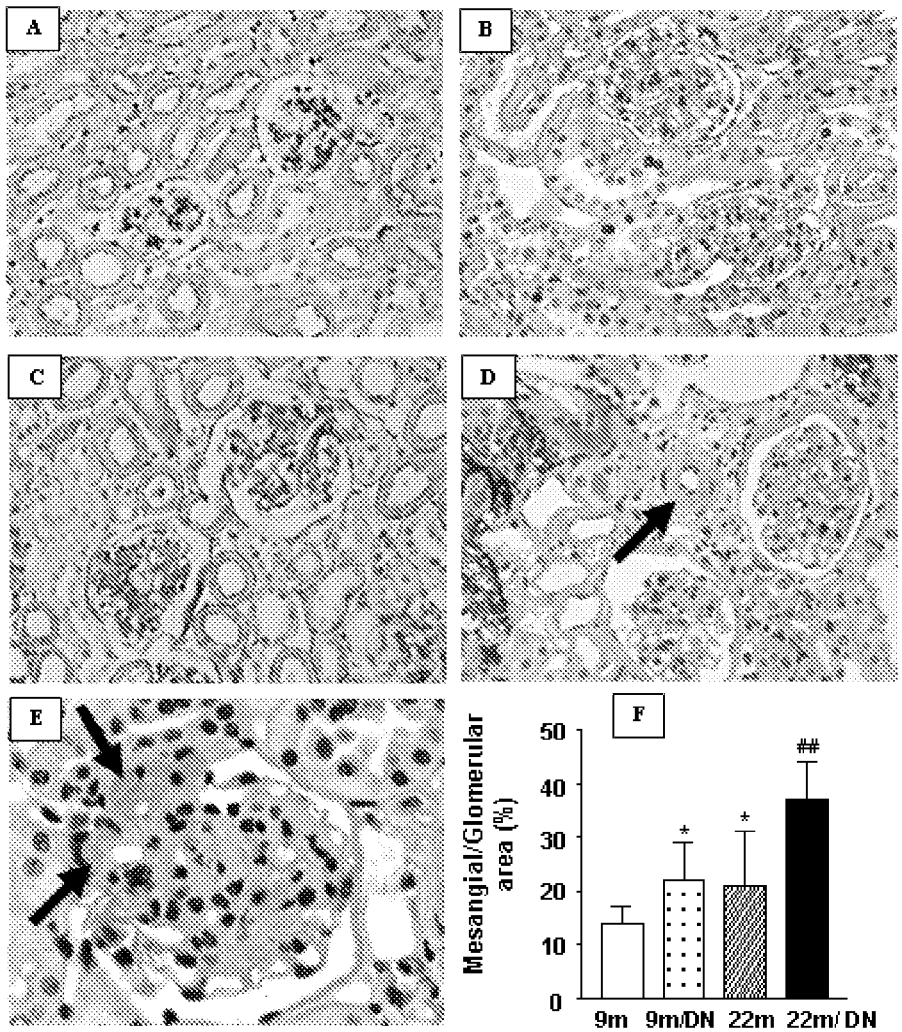
FIGS. 8A-8F show severe nephropathy in 22 month-old diabetic mice.
Figures 9A, 9B, 9C, 9D:
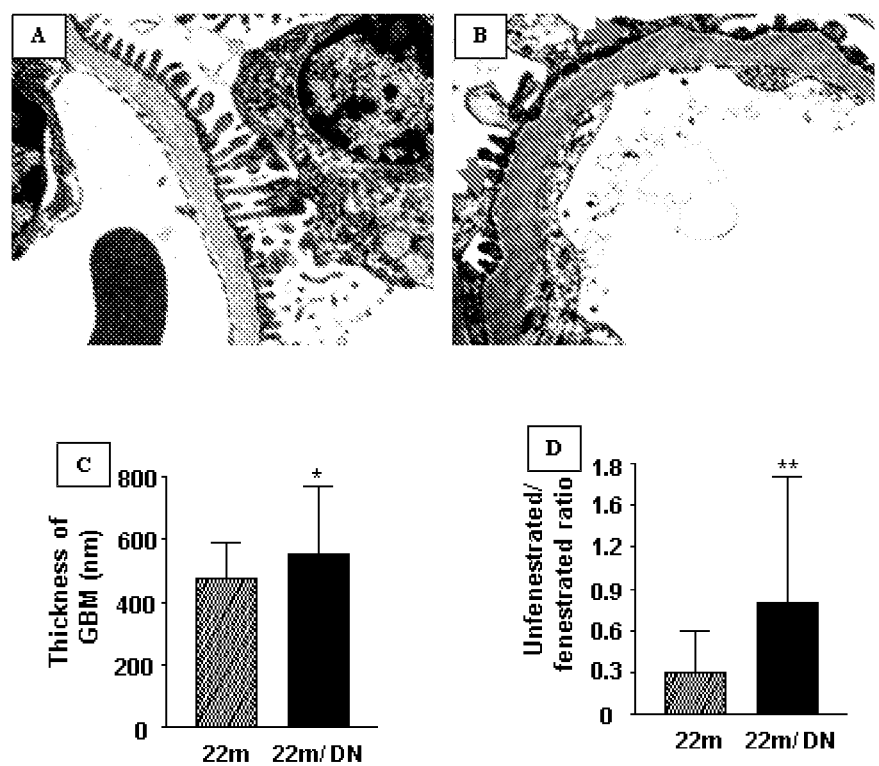

Renal Histology:

9 month-old diabetic mice exhibited diffuse, mild glomerular lesions, characterized by glomerular hypertrophy and a small increase in the mesangial areas (FIGS. 8A, 8G). There were no tubulointerstitial lesions in 9 month-old diabetic mice. 22 month-old non-diabetic mice had prominent glomerular hypertrophy, a slight increase in the mesangial areas, and a largely normal tubulointerstitium (FIG. 8C). In contrast, 22 month-old non-diabetic diabetic mice developed severe glomerular and tubulointerstitial lesions (FIGS. 8D-F) and there was an increase in overall glomerular cell number. The mesangium was diffusely and markedly enlarged (FIGS. 8D, 8E, 8G). The basement membranes of Bowman's capsules were markedly thickened and duplicated. Obsolescent glomeruli were relatively frequently encountered, compared to age-matched 22 month-old non-diabetics. There was a decrease in the size of most vascular spaces, although dilated loops were occasionally encountered. The walls of afferent and efferent arterioles were noticeably thickened by a prominent increase in homogenous PAS positive materials, i.e., hyalinosis in both the afferent and efferent arteriolar walls (FIG. 8E). The walls of small arterioles had a significantly increased width due to fibrosis and/or an increased cell number, including foam cells (FIG. 8D). Morphometric analysis revealed that the glomerular volume was increased in 9 month-old diabetic mice and was further increased in 22 month-old non-diabetic and 22 month-old diabetic mice. There was glomerular volume not difference between 22 month-old diabetic mice ($3.8\pm0.7\times10^5$ µm$^3$) and non-diabetic 22 month-old non-diabetics ($3.3\pm0.7\times10^5$ µm$^3$). However, the mesangial area was significantly enlarged (FIG. 8F) and there was an apparent increase in thickness of glomerular basement membrane in 22 month-old diabetic mice (FIGS. 8D, 8E). Examination of electron micrographs revealed that the thickness of glomerular basement membranes was generally, but irregularly, increased in 22 month-old mice and further increased in 22 month-old diabetic mice (FIGS. 9A, 9B). Fusion of podocyte foot processes was seen in some peripheral loops of 22 month-old diabetic mice (FIG. 9B, arrows). The unfenestrated area in glomerular capillary endothelial cells was significant increased in 22 month-old diabetic mice (FIG. 9B). Tubular atrophy and loss of tubular structures were prominent changes, in association with expansion of the interstitial space due to loss of tubules, fibrosis, and an extensive, diffuse infiltration of inflammatory cells (FIG. 9F).

Figures 10A, 10B:
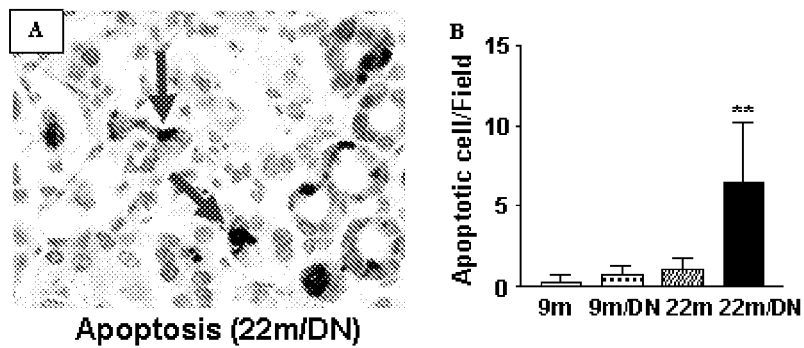
FIGS. 10A-10B show apoptosis in the kidneys of 22 month-old diabetic mice.

Apoptosis:

To further characterize the lesions and explore the underlying mechanism(s) of increased cellular injury in 22 month-old diabetic mice, the number of apoptotic cells in kidneys was determined by TUNEL staining. There was a prominent increase in the number of apoptotic cells in 22 month-old diabetic kidneys (FIGS. 10A, 10B). Dead cells were mostly located in tubules and the interstitium. In contrast, TUNEL-positive cells were rarely found in 9 month-old non-diabetic kidneys and were only occasionally seen in 9 month-old diabetic kidneys. There were few apoptotic cells in 22 month-old non-diabetic kidneys (FIG. 10B).

Figures 11A, 11B:
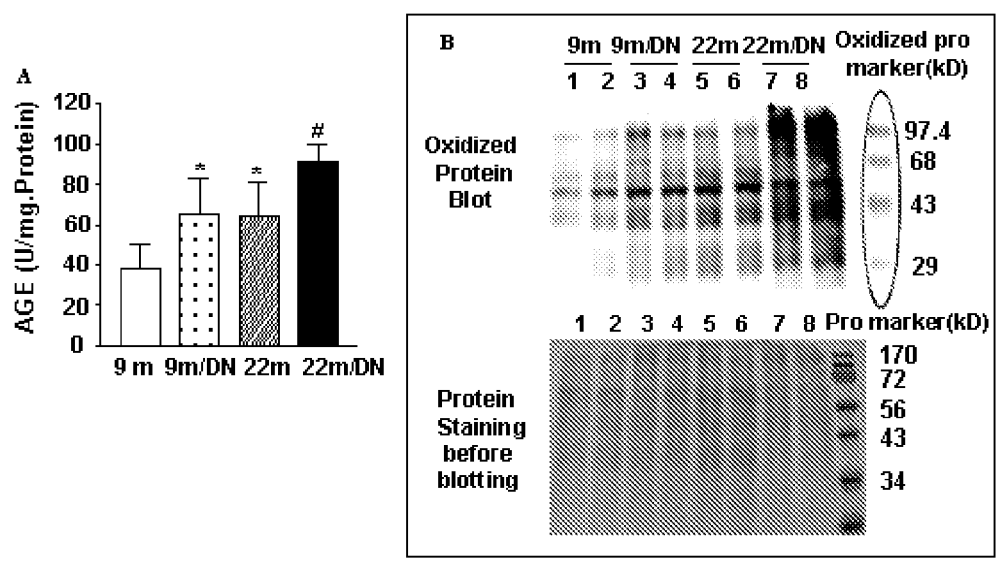
FIGS. 11A-11L shows the oxidative stress in the kidneys of 22 month-old diabetic mice.

Oxidative Stress:

Since oxidative stress is closely associated with aging and is an important cause of apoptotic cell death, the levels of oxidative stress in 22 month-old diabetic kidneys was examined. Kidney AGEs levels were elevated in 9 month-old diabetic and 22 month-old non-diabetic mice compared to 9 month-old non-diabetic mice. Interestingly, the levels of kidney AGEs were comparable between 9 month-old diabetic and non-diabetic 22 month-old non-diabetic mice (FIG. 11A). However, the levels of AGEs in kidneys of 22 month-old diabetic mice were higher than either 9 month-old diabetic or 22 month-old non-diabetic mice (FIG. 11A).

The amount of oxidized proteins in kidney was increased in the kidneys of 9 month-old diabetic (FIG. 11B; lanes 3, 4) and 22 month-old non-diabetic mice (FIG. 11B; lanes 7, 8) as compared to 9 month-old non-diabetic mice (FIG. 11B; lanes 1, 2). The increase was comparable between kidneys of 22 month-old non-diabetic mice and 9 month-old diabetic mice. The amount of oxidized proteins was greatest in kidneys of 22 month-old diabetic mice (FIG. 11B; lanes 7, 8).

Figures 11C, 11D, 11E, 11F, 11G, 11H, 11I, 11J:
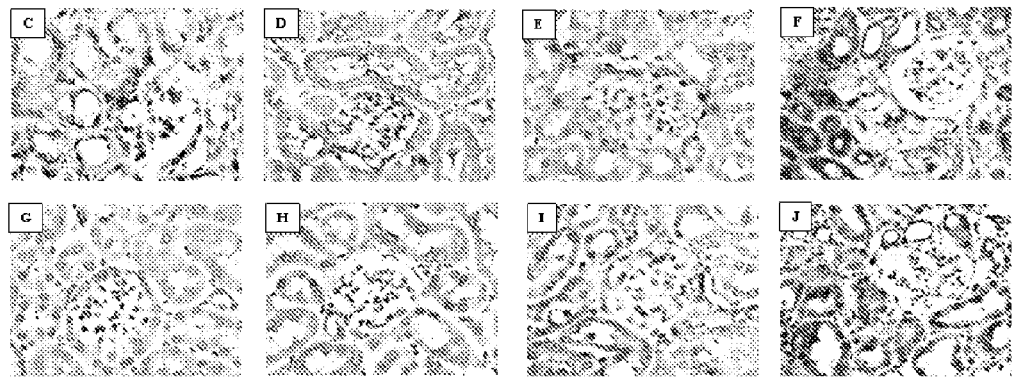

Protein nitration, as demonstrated by staining tissue with an anti-nitrotyrosine antibody, was barely visible in the kidneys of 9 month-old non-diabetic mice but was increased in the kidneys of 9 month-old diabetic and 22 month-old non-diabetic mice (FIGS. 11C-11E). A more prominent increase in the intensity of nitrotyrosine staining was found in 22 month-old diabetic kidneys, particularly in the cytoplasm of tubular cells (FIG. 11F).

Figures 11K, 11L:
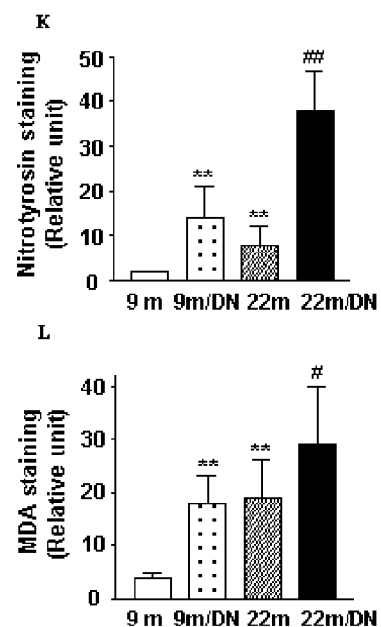

Lipid peroxidation, as indicated by MDA staining, was most evident in tubules (FIGS. 11G-11J). MDA staining in 9 month-old kidneys was mild compared to 9 month-old diabetic and 22 month-old non-diabetic kidneys (FIGS. 11G, 11H, 11I). Intense staining was present in tubular cells of 22 month-old diabetic kidneys (FIG. 11J). Digital quantitation of the intensity of immunostaining further supported an increase in nitrotyrosin and MDA staining in 22 month-old diabetic kidneys (FIGS. 11K, 11L).

Figures 12A, 12B, 12C, 12D, 12E, 12F:
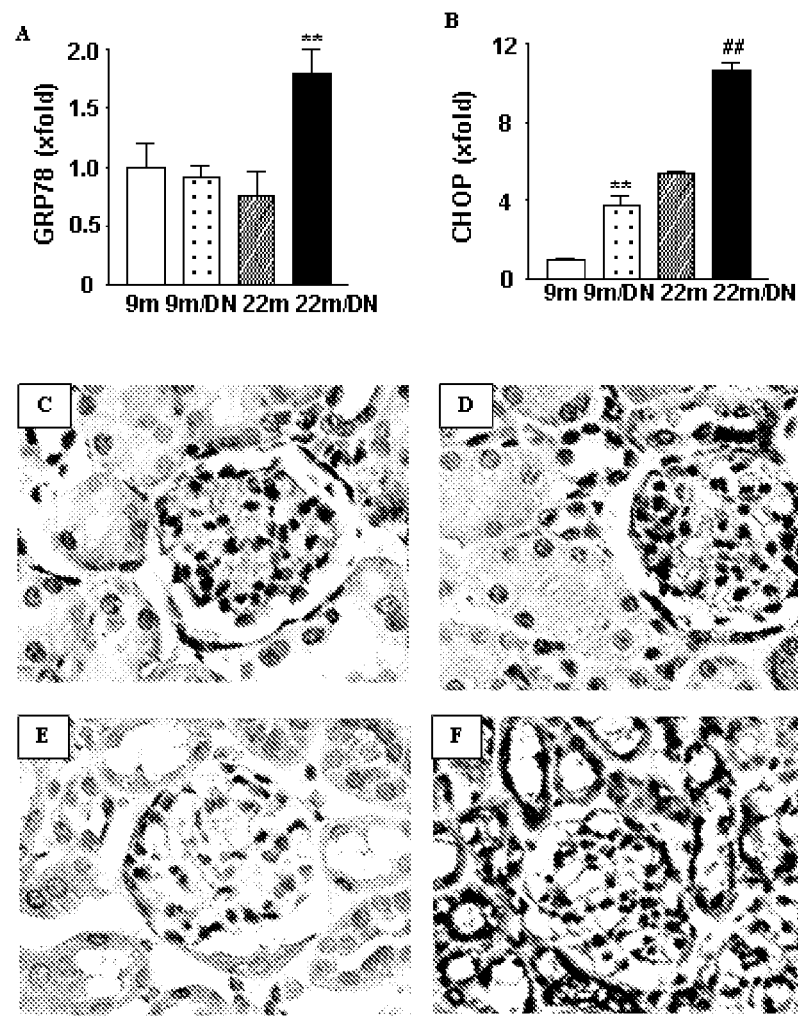

ER Stress:

ER stress has been shown to be present in the tubulointerstitium of patients with progressive diabetic nephropathy. Three regulatory pathways, namely PERK-eIF2α, IRE1 (Inositol requiring enzyme 1)-XBP-1, and ATF6 (activating transcription factor 6), are critical in the ER stress response. The activation of ATF6 increases GRP78 and the activation of PERK-eIF2α increases CHOP transcription. CHOP mRNA levels were 2-fold increased in 9 month-old diabetic and 22 month-old non-diabetic mice, compared to 9 month-old non-diabetic mice. GRP78 and CHOP mRNA levels were elevated about 2-fold in the kidneys of 22-month old diabetic mice compared to the kidneys of 9 month-old diabetic and 22 month-old non-diabetic mice (FIGS. 12A, 12B). The staining of phospho-PERK, which is normally present in glomeruli as well as in some of tubules of 9 month-old mice, was not different between the kidneys of 9 month-old non-diabetic and 9 month-old diabetic mice (FIGS. 12C, 12D). Phospho-PERK staining was visibly decreased in kidneys of 22 month-old non-diabetic mice (FIG. 12E). However, nearly 80% of cells in renal cortex showed positive staining in 22 month-old diabetic mice (FIG. 12F). Phospho-PERK phosphorylates eIF2α. Surprisingly, the staining of phospho-eIF2α was strong in 22 month-old non-diabetic kidneys even though their phospho-PERK staining was weak, evidencing that increased eIF2α phosphorylation may be caused by kinase(s) other than PERK. There were no differences in phospho-eIF2α staining between the kidneys of 9 month-old non-diabetic mice (FIG. 12G) and 9 month-old diabetic mice (FIG. 11H). Phospho-eIF2α staining was intensively increased in many kidney cell types of 22 month-old diabetic mice (FIG. 12I).

Figures 13A, 13B, 13C, 13D:
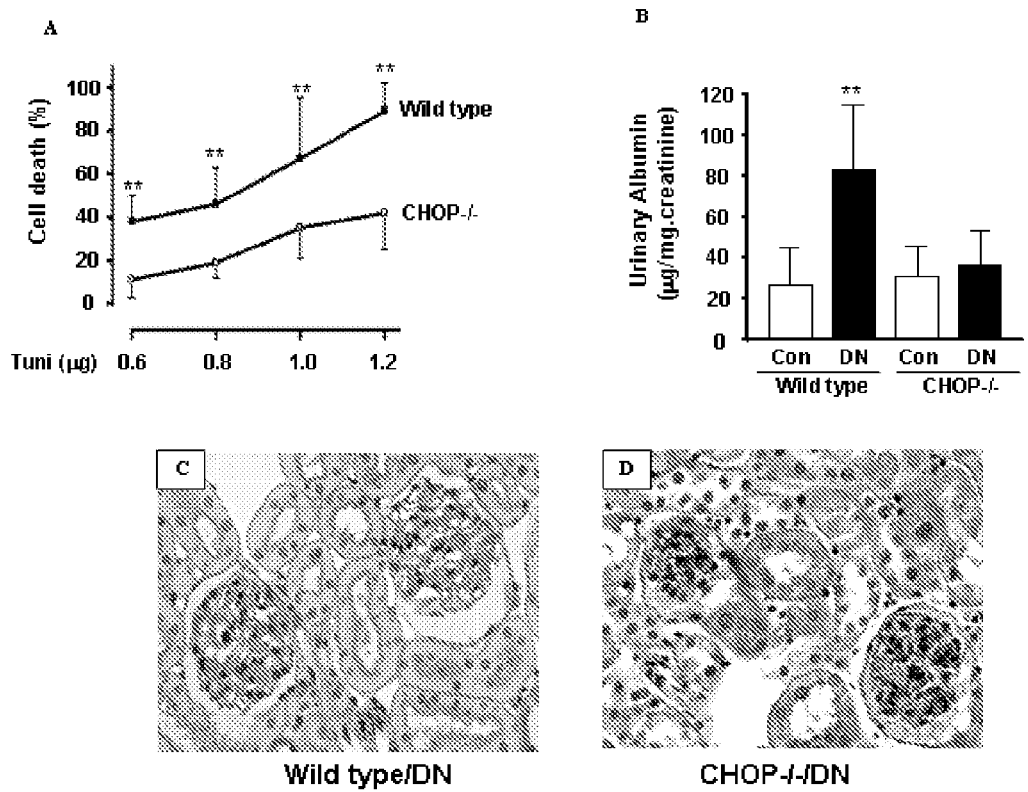
FIGS. 13A-13D show CHOP$^{-/-}$ diabetic mice and CHOP$^{-/-}$ proximal tubular cells.

Both oxidative stress and ER stress are known causes of cell death. A dose dependent increase in apoptotic cell death was found in proximal tubular cells when cells were exposed to $H_2O_2$ to induce oxidative stress and to tunicamycin to induce ER stress (FIG. 13A). Thus, increased oxidative stress and the presence of ER stress may be one of the causes of increased cell death in 22 month-old diabetic kidneys.

CHOP in ER Stress-Induced Cell Death, and in Diabetic Nephropathy:

CHOP is an important factor in ER stress-induced cell death. Since CHOP mRNA levels were most increased in 22 month-old diabetic kidneys, we asked if CHOP contributed to ER stress induced proximal tubular cell death. Proximal tubular cells from CHOP$^{-/-}$ and wild type mice were treated with 0.6-1.2 μg/ml of tunicamycin. 0.6 μg/ml and 1.2 μg/ml of tunicamycin caused 38% and 89% cell death, respectively, in wild type proximal tubular cells (FIG. 13A). A 50% reduction in cell death was found in CHOP$^{-/-}$ proximal tubular cells at all levels of tunicamycin treatment.

To further explore a role of CHOP in diabetic nephropathy, diabetes was induced by streptozotocin treatment in young CHOP knock-out and wild type mice. The development of diabetes in wild type mice resulted in a 2-fold increase in urine albumin excretion (FIG. 13B). However, diabetic CHOP$^{-/-}$ mice did not develop albuminuria. A moderate increase in mesangial area was present in some of glomeruli of wild type diabetic mice (FIG. 13C) while glomeruli were largely normal in CHOP$^{-/-}$ diabetic mice (FIG. 13D).

Figures 3A, 3B, 3C, 3D, 3E, 3F:
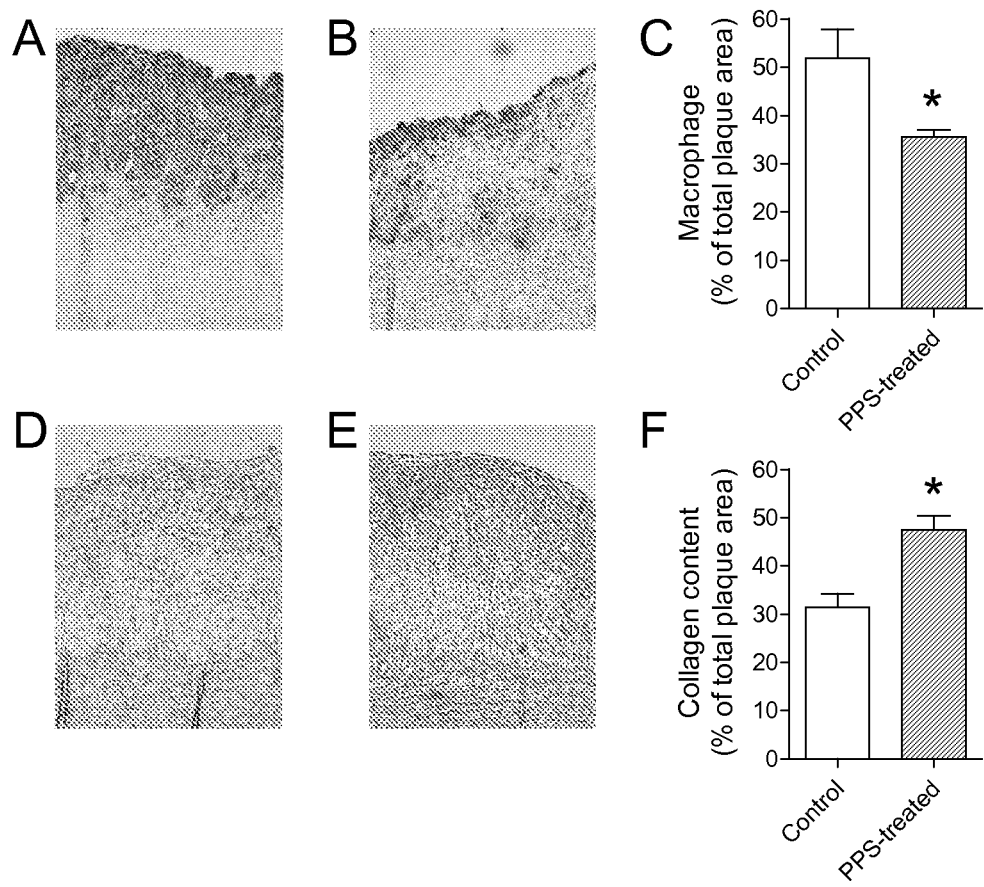
FIGS. 3A-3B show representative micrographs of cross sections of aortic arch from WHHL rabbits fed a HC-diet 75 days stained immunohistochemically with RAM-11 antibody to detect macrophage infiltration.
FIG. 3C: Quantification of macrophage infiltration in aortic cross sections. White bars: WHHL rabbits fed a HC-diet for 75 days; Diagonal hatched bars: WHHL rabbits fed a HC-diet for 75 days, on day 45 PPS was added to the drinking water and continued for the remaining 30 days.
FIGS. 3D-3E show representative micrographs of cross sections of aortic arch from WHHL rabbits fed a HC-diet 75 days stained with Sirius red to quantify collagen content.
FIG. 3F: Quantification of collagen content in aortic cross sections. White bars: WHHL rabbits fed a HC-diet for 75 days; Diagonal hatched bars: WHHL rabbits fed a HC-diet for 75 days, on day 45 PPS was added to the drinking water and continued for the remaining 30 days. Quantification of macrophage infiltration and collagen content in atherosclerotic lesions was performed by computer-aided morphometric analysis as detailed in the Materials and Methods section. *P<0.05.
Figures 14A, 14B, 14C, 14D, 14E, 14F, 14G:
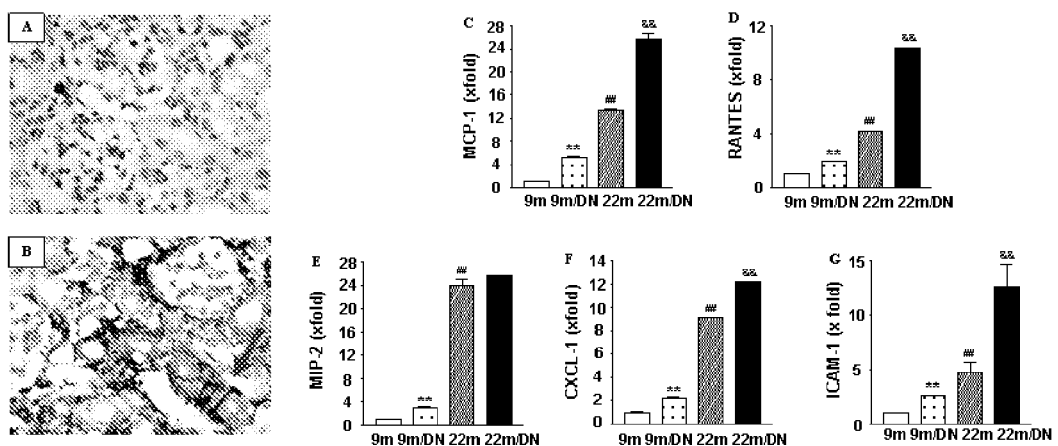
FIGS. 14A-14K show proinflammatory gene expression and immunostaining for monocyte/macrophage and NF-κB. The presence of monocyte/macrophages in the kidney was evaluated by F4/80 staining Positive staining is barely visible in 9 month-old non-diabetic, 9 month-old diabetic and 22 month-old non-diabetic kidneys (FIG. 14A). Extensive staining is present in the tubulointerstitium of 22 month-old diabetic mice (FIG. 14B). mRNA levels: MCP-1 (FIG. 14C), RANTES (FIG. 14D), MIP-2 (FIG. 14E), CXCL-1 (FIG. 14F), and ICAM-1 (FIG. 14G) in kidneys of 9 month-old non-diabetic (9 m), 9 month-old diabetic (9 m/DN), 22 month-old non-diabetic (22 m), and 22 month-old diabetic mice (22 m/DN) were determined by real-time PCR and corrected by β-actin mRNA levels. The levels in the kidneys of 9 month-old non-diabetic mice were arbitrarily defined as 1. MCP-1, MIP-2, and CXCL-1 mRNA levels were significantly increased in the kidneys of 9 month-old diabetic mice and further increased in the kidneys of 22 month-old non-diabetic mice. **$p<0.01$, vs., 9 m; ##$p<0.01$, vs. kidneys from 9 m/DN. The levels of MCP-1, RANTES, CXCL-1, and ICAM-1 were increased more in the kidneys of 22 month-old diabetic mice compared to 22 month-old non-diabetic mice. &&$p<0.01$, vs. 22 m. Nuclear phosphorylated NF-κB (p65 (Ser276) staining, a marker for NF-κB activation, was positive in cells of the kidney in 9 month-old non-diabetic (FIG. 14H, ×500, arrow), 9 month-old diabetic (FIG. 14I, ×500), 22 month-old non-diabetic (FIG. 14J, ×500), and 22 month-old diabetic mice (FIG. 14K, ×500). While positive cells are not seen in the glomeruli of 9 month-old non-diabetic, they are present in 9 month-old diabetic, 22 month-old non-diabetic (arrows), and 22 month-old diabetic glomeruli. Positive cells are abundant in every field of kidneys of 22 month-old diabetic mice, including infiltrating cells.
Figure 14:
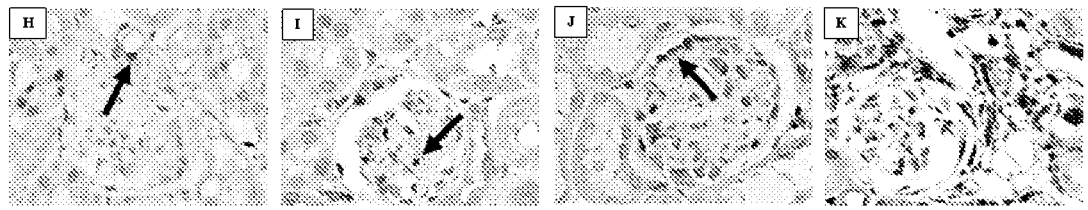

Inflammation:

As noted above, there is a prominent increase in inflammatory cells in tubulointersitium of 22 month-old diabetic mice (FIG. 3F). Whereas few macrophages were present in 9 month-old non-diabetic mice (FIG. 14A) anti-F4/80 staining showed that macrophages accounted for a significant portion of the infiltrating inflammatory cells in 22 month-old diabetic kidneys (FIGS. 14A-14K). Macrophages were rarely seen in the kidneys of 9 month-old non-diabetic, 9 month-old diabetic, and 22 month-old non-diabetic mice. There was an increase in expression of MCP-1, RANTES, MIP-2, CXCL-1, and ICAM-1 mRNAs in the kidneys of 9 month-old diabetic mice compared to kidneys of 9 month-old non-diabetic mice (FIGS. 14C-14G). However, the increase was further augmented in the kidneys of 22 month-old non-diabetic mice (the levels of MCP-1, RANTES, MIP-2, CXCL-1, and ICAM-1 mRNA were 2.6-fold, 2.1-fold, 7.8-fold, 9.2-fold, and 1.8-fold respectively higher than that in the kidneys of 9 month-old diabetic mice). These pro-inflammatory chemokines and adhesion molecule mRNA levels were further elevated in the kidneys of 22 month-old diabetic mice, except for MIP-2 (FIG. 14E), resulting in ~25-fold increases over 9 month-old non-diabetic mice (FIGS. 14C, 14D, 14F, 14G). Nuclear phosphorylated NF-κB staining, an indication of NF-κB activation was present in interstitial capillary endothelial cells, parietal epithelial cells, and some cells of distal tubules and collecting ducts in the kidneys of normal 9 month-old non-diabetic mice (FIG. 14H). The number of nuclear NF-κB positive cells, localized mostly to glomeruli, was moderately increased in the kidneys of 9 month-old diabetic and 22 month-old non-diabetic mice (FIGS. 14I, 14J). The number was markedly increased in the tubulointerstitium of 22 month-old diabetic mice (FIG. 14K).

Figures 15A, 15B:
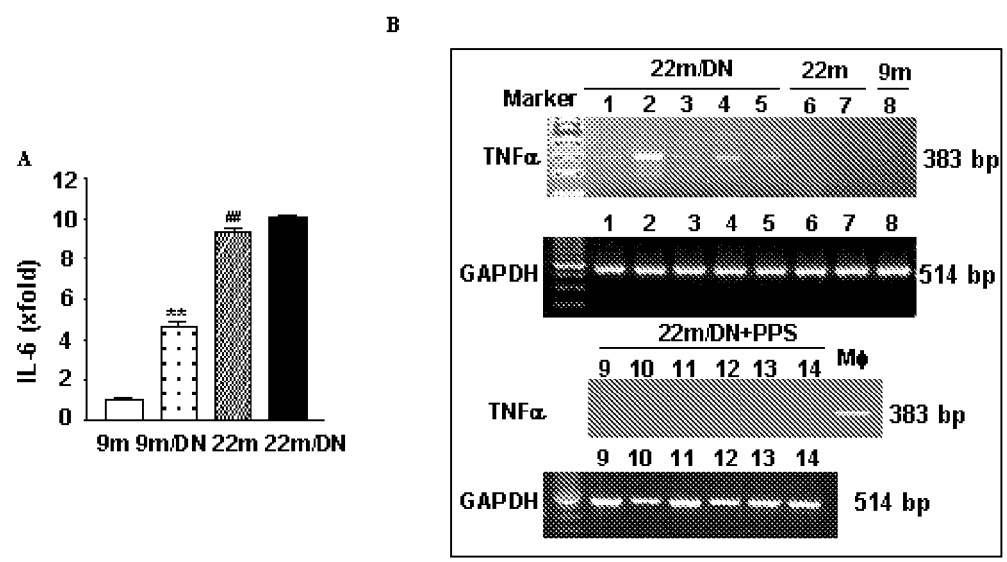
FIG. 15A: IL-6 expression: IL-6 mRNA levels were increased in 9 month-old diabetic (9 m/DN) kidneys and further increased in 22 month-old non-diabetic (22 m) and 22 month-old diabetic kidneys (22 m/DN). $p<0.01$, vs., 9 m; ##$p<0.01$, vs., 9 m/DN.
FIGS. 15B-15J: PPS suppressed TNFα expression in the kidneys of 22 month-old diabetic mice and decreased TNFα stimulated inflammation in the proximal tubular cell line.
Figures 15C, 15D, 15E, 15F, 15G, 15H, 15I, 15J:
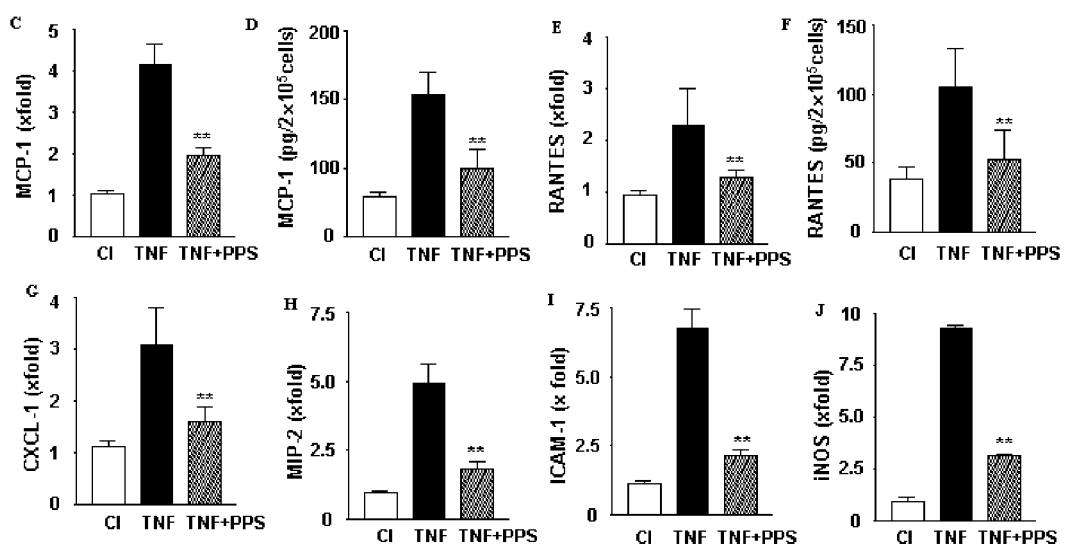

IL-6 and TNFα:

The cause(s) of chronic inflammation in the kidneys of 22 month-old diabetic mice were examined by evaluating the expression of IL-6 and TNFα. IL-6 mRNA levels were ~5-fold increased in the kidneys of 9 month-old diabetic mice compared to the kidneys of 9 month-old non-diabetic mice (FIG. 15A). The levels were further increased in the kidneys of 22 month-old non-diabetic mice and 22 month-old diabetic mice (FIG. 15A). However, the levels of IL-6 mRNA in the kidneys of 22 month-old diabetic and 22 month-old non-diabetic mice did not differ (FIG. 15A). Circulating TNFα levels were elevated in 4 out of 11 22 month-old diabetic mice but the average levels were not statistically different among 9 month-old non-diabetic, 9 months-old diabetic, 22 month-old non-diabetic, and 22 month-old diabetic mice. However, TNFα mRNA expression was present and increased in the kidneys of 22 month-old diabetic mice (FIG. 15B). The responses in parenchymal cells in vitro was different, in that TNFα stimulated MCP-1, RANTES, CXCL-1, MIP-2, ICAM-1, and iNOS mRNA expression in proximal tubular cells in vitro, as well as in podocytes and mesangial cells (FIGS. 15C-15J). TNFα also stimulated MCP-1 and RANTES production in these cells (FIGS. 15D, 15F).

Figures 16A, 16B, 16C:
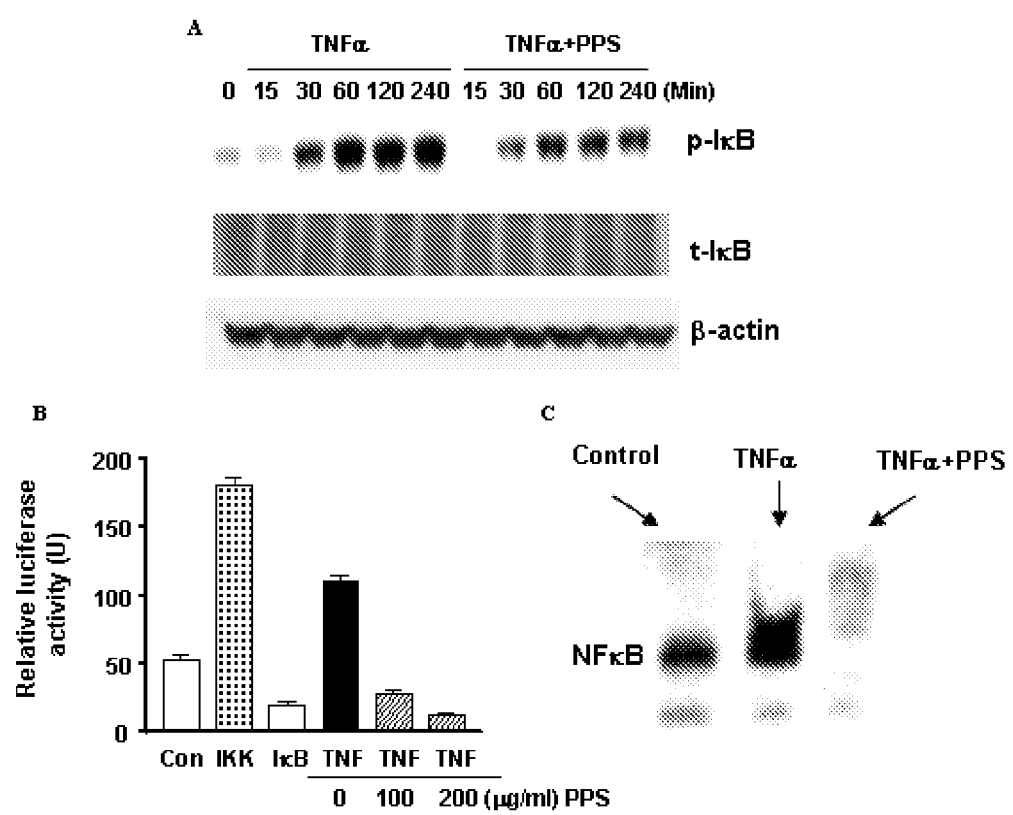
FIGS. 16A-16C: PPS suppressed TNFα stimulated NF-κB activation in cells from a proximal tubular cell line: Cells were pre-treated without or with PPS for half an hour before the addition of TNFα.

Inhibition of TNFα action by PPS via NF-κB:

Since NF-κB and MAPKs pathways play are involved in TNFα action, the effects of PPS on TNFα stimulated NF-κB and MAPKs activation were examined. When proximal tubular cells were treated with PPS before TNFα stimulation, the levels of IκB phosphorylation were decreased 40-60% (FIG. 16A). The levels of total IκB did not fluctuate, but p-IκB increased at 30 and 60 minutes in proximal tubular cells after TNFα stimulation (FIG. 16A). The NF-κB luciferase reporter assay showed that PPS treatment dependently decreased TNFα stimulated NF-κB transcriptional activity in proximal tubular cells (FIG. 16B). Furthermore, PPS treatment nearly completely blocked TNFα-induced increase in NF-κB DNA binding activity (FIG. 16C). PPS treatment also suppressed TNFα-stimulated ERK1/2 phosphorylation in proximal tubular cells.

Figures 17A, 17B, 17C, 17D:
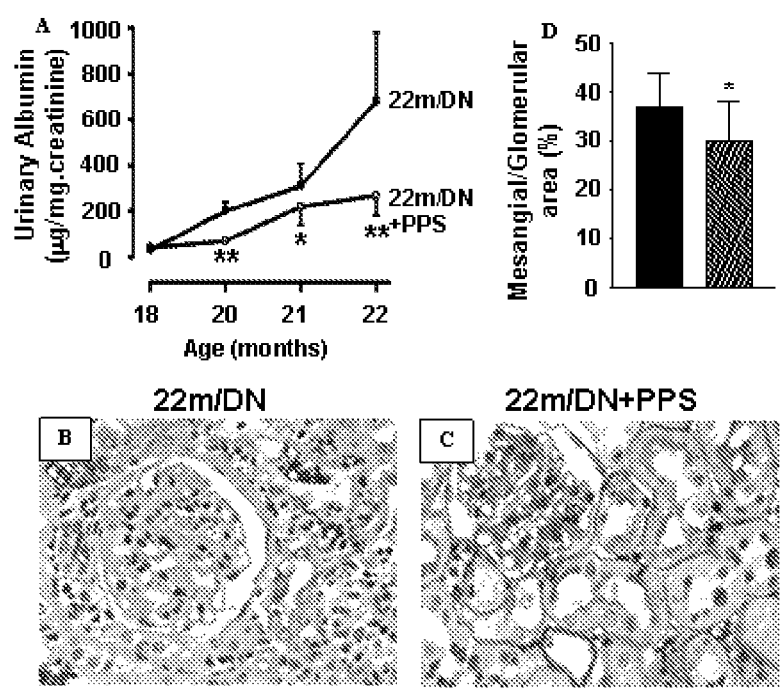
Figures 17E, 17F, 17G, 17H, 17I, 17J:
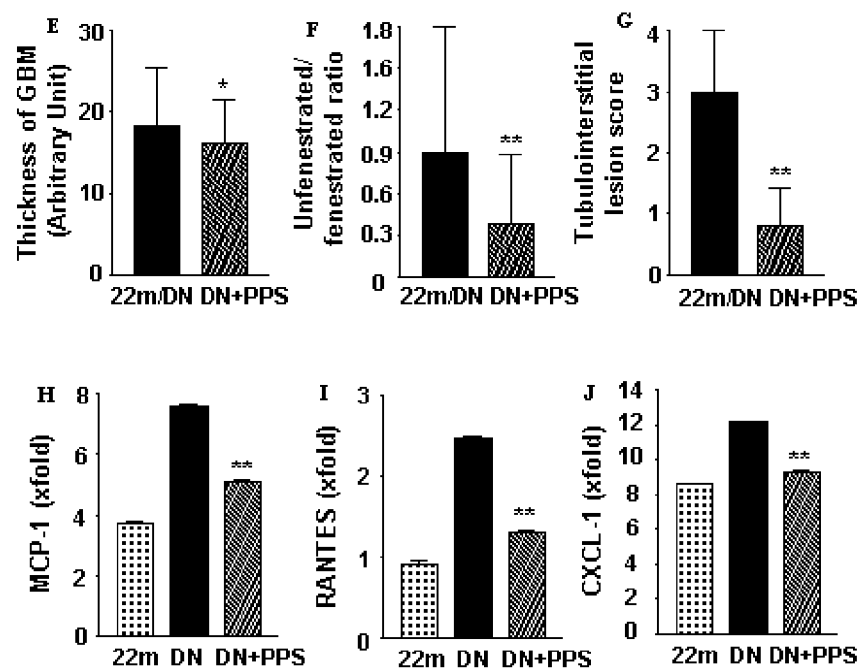
FIGS. 17H, 17I, 17J: Real-time PCR quantitation of mRNA levels of MCP-1 (FIG. 17H), RANTES (FIG. 17I), and CXCL-1 (FIG. 17J) in renal cortices of 22 month-old non-diabetic (22 m), 22 month-old diabetic (DN), and PPS treated 22 month-old diabetes mice (DN+PPS). PPS treatment reduced these mRNAs to the levels similar to 22 month-old non-diabetic. $P<0.01$, vs., DN.
Figures 17K, 17L:
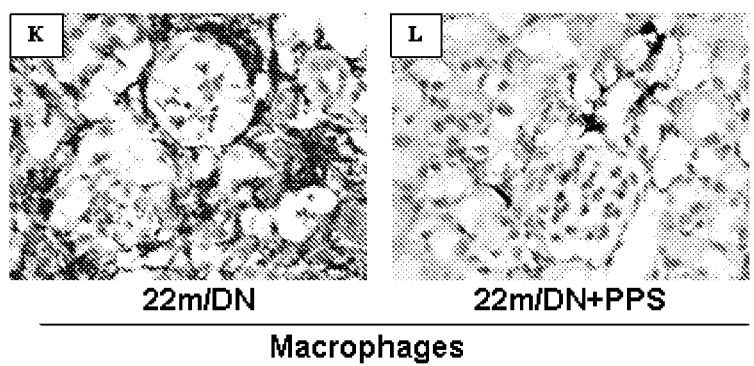
FIGS. 17K, 17L: Extensive macrophage infiltration in untreated 22 month-old diabetic kidneys as demonstrated by F4/80 immunostaining was largely prevented by PPS treatment (FIG. 17K, untreated.
Figures 17M, 17N:
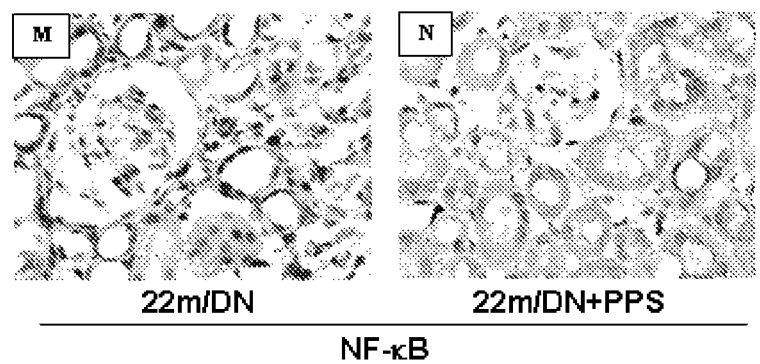

PPS treatment blunted the rise in albuminuria and decreased inflammation and the severity of renal lesions in 22 month-old diabetic mice: PPS treatment slowed the progressive increase in urine albumin excretion in 22 month-old diabetic mice (FIG. 17A), and completely prevented the upregulation of TNFα expression in the kidneys of 22 month-old diabetic mice (FIG. 15B). This was associated with decreased MCP-1, RANTES, and CXCL-1 mRNA levels and with a nearly complete absence of macrophage infiltration and a substantially less NF-κB activation in the kidneys of PPS treated 22 month-old diabetic mice (FIG. 17H-N). The glomerular lesions, including the expansion of mesangial areas, increase in thickness of basement membranes, and loss of glomerular endothelial fenestrations were decreased by PPS treatment (FIG. 17B-17E). Most strikingly, PPS treatment nearly completely prevented the development of tubulointerstitial lesions in 22 month-old diabetic mice by ~80% (FIG. 17G).

PPS Treatment Preserved Renal Function:

Serum creatinine levels were significantly elevated in untreated 22 month-old diabetic mice as compared age-matched non-diabetic mice (p<0.05) (Table 2). PPS treatment prevented the increase in serum creatinine (0.118±0.02 mg/dL, vs., age-matched non-diabetic mice, 0.109±0.03 mg/dL, p>0.05).

Figure 18:
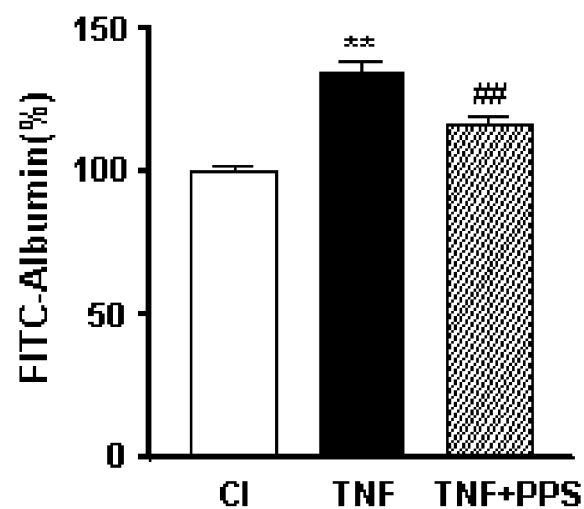
FIG. 18 shows that PPS decreases TNFα stimulated albumin permeability in podocytes in vitro. Monolayers of podocytes were treated with TNFα (20 ng/ml), PPS (400 μg/ml), or PPS plus TNFα, and the amount of FITC-labeled BSA that passed through the cell layer was quantitated. The value of albumin flux through monolayer without TNFα or PPS treatment was arbitrarily defined as 100%. TNFα increased the flux of FITC-labeled BSA, and PPS inhibited the flux by 34%. **$p<0.01$, vs., non-diabetic; ##$p<0.01$, vs., cells treated with TNFα alone.

PPS Decreased the TNFα-Induced Increase in Albumin Permeability in Podocytes in Vitro:

The amount of FITC-labeled albumin that passed through a monolayer of podocytes on a membrane was increased by 34% at 2 hours after TNFα treatment (FIG. 18). This increase was reduced by nearly 60% in the presence of PPS pretreatment.

TABLE 2

|  | Young mice (9 months) | | Old mice (22 months) | | |
| --- | --- | --- | --- | --- | --- |
|  | Control (n = 6) | Diabetic (n = 7) | Control (n = 10) | Diabetic (n = 11) | PPS (n = 10) |
| Body weight (g) | 23.4 ± 2.8 | 21.4 ± 3.2 | 25.7 ± 1.4 | 24.4 ± 0.5 | 24.1 ± 1.3 |
| Heart weight (mg) | 116 ± 11 | 121 ± 12 | 167 ± 19 | 169 ± 23 | 170 ± 14 |
| Kidney weight (mg) | 197 ± 16 | 194 ± 22 | 218 ± 11 | 225 ± 19 | 221 ± 23 |
| Glucose (mg/dL) | 124 ± 28 | 397 ± 42 | 106 ± 34 | 301 ± 36 | 332 ± 68 |
| BUN (mg/dL) | 19.1 ± 4.5 | 20.6 ± 7.3 | 15.8 ± 2.5 | 24.5 ± 8.9 | 21.3 ± 5.6 |
| Scr (mg/dL) | 0.119 ± 0.01 | 0.121 ± 0.04 | 0.109 ± 0.03 | 0.138 ± 0.02* | 0.118 ± 0.02 |

Discussion

The kidneys of aged humans and mice are more susceptible to injury than in the younger individuals. In addition, older patients who develop acute kidney injury, particularly those who already had reduced renal function, are more likely to progress to end stage renal disease. The reasons for the increased susceptibility to injury and reduced ability to regain previous levels of renal function are unknown. However, the increased oxidant stress and inflammation in aging may render the aged kidney less able to deal with subsequent renal injuries, with resultant cell death rather than repair. This hypothesis was tested herein, in 22 month-old C57B6 mice, in that C57B6 mice progressively develop reduced anti-oxidant reserves, increased expression of inflammatory cytokines, and insulin resistance with aging (Zheng F, et al., Am J Pathol 2004, 165:1789-1798). Furthermore, glomerular mesangial cells from aged mice show stable phenotypic changes in vitro consisting of increased baseline ROS and increased production of inflammatory cytokines and extracellular matrix. These biochemical changes are reflected in histologic changes consisting of slowly progressive renal hypertrophy beginning at 18 months of age, mild to moderate mesangial expansion at 22 months, moderate albuminuria and tubulointerstitial lesions at 24-26 months, and severe albuminuria and glomerular and tubulointerstitial lesions at 30 months of age.

Eight month-old C57B6 mice were shown previously, to be relatively resistant to the development of albuminuria and histologic features of diabetic nephropathy. In contrast, the current study shows that 22 month-old mice developed severe albuminuria, severe renal injury and elevated serum creatinine levels after with the induction of hyperglycemia. This accentuated response is similar to the accelerated lesions after unilateral nephrectomy in C57B6 mice of a similar age. Thus, aging predisposes otherwise resistant mice to the development of progressive renal disease. This is similar to the situation in older patients subjected to stress during hospitalization.

The renal lesions in 22 month-old diabetic mice including hyalinosis in arteriolar walls, increased thickness of glomerular basement membranes, reduced glomerular fenestration, expansion of mesangial area, and severe tubulointerstitial lesions, are features typical of diabetic nephropathy in humans. More importantly, the incidence of diabetes and diabetic nephropathy increases with age in humans. Thus, the use of 22 month-old diabetic C57B6 mice may allow the elucidation of the pathways important in the mechanisms underlying changes in the kidney induced by hyperglycemia in aging.

Oxidative stress is likely an important contributor to diabetes induced severe renal disease in aging mice. There was increased oxidative stress and the accumulation of AGEs in the kidneys of 22 month-old mice. While oxidative stress was also present in 9 month-old diabetic kidneys, the level was comparable to 22 month-old non-diabetic mice. These data are consistent with the fact that the degree and distribution of histologic lesions were similar in the kidneys of 22 month-old non-diabetic and 9 month-old diabetic mice in the current study. The addition of hyperglycemia to 22 month-old mice led to further elevations in the level of oxidative stress, which may have contributed to the severity of the lesions in 22 month-old diabetic mice by inducing or increasing apoptotic cell death. The tubulointerstitial compartment showed the most prominent increase in oxidative stress, as demonstrated by MDA and nitrotyrosine immunohistochemical staining. This was also the site of the greatest number of apoptotic cells. This association, together with the finding that hydrogen peroxide increased proximal tubular cell death in vitro, adds support to a role for oxidative stress in tubular cell death.

ER stress is another important form of cell stress that is critically involved in several acute and chronic diseases. GRP78 is an important marker for ER stress. Since GRP78 mRNA levels were increased in 22 month-old diabetic kidneys and this increase was associated with elevated levels of phosphorylated PERK and phosphorylated eIF2α, these data suggest that chronic ER stress is present. ER stress has also been demonstrated in the tubulointerstitial compartment of patients with progressive diabetic nephropathy. The current in vitro and in vivo studies show that the induction of ER stress in proximal tubular cells caused a dose dependent increase in cell death. Thus, ER stress may be another contributor to the increased number of apoptotic cells in the kidneys of 22 month-old diabetic mice. It is unknown if ER stress is also present in the kidneys of 9 month-old diabetic mice, because even though the levels of CHOP mRNA were increased, the levels of GRP78 were unchanged. CHOP transcription is increased in ER stress due partly to the activation of PERK-eIF2α pathway. Increased levels of CHOP are critical to the induction of apoptosis by ER stress. Since 22 month-old diabetic kidneys had the most significant increase in CHOP expression, we examined the contribution of CHOP to ER stress induced cell death in proximal tubular cells and found that proximal tubular cells from CHOP deficient mice were resistant to ER stress-induced cell death. This result is consistent with CHOP$^{-/-}$ mice which are resistant to acute ER stress kidney injury. Importantly, the results herein, found that CHOP deficient mice were resistant to diabetic nephropathy.

Chronic tubulointerstitial lesions, characterized by inflammation and fibrosis, are a hallmark of progressive kidney diseases, including kidney aging and diabetic nephropathy. Severe tubulointerstitial lesions were present in the kidneys of aged diabetic mice. The underlying cause(s) of chronic tubulointerstitial inflammation is not clear. Since the data herein found that the upregulation of MCP-1, CXCL-1, and MIP-2 mRNA expression in the kidneys of 22 month-old non-diabetic evidence that these changes in the expression of inflammatory cytokines in parenchymal cells may play a role in the recruitment of inflammatory cells. The expression of MCP-1, CXCL-1, RANTES and ICAM-1 was further increased in the kidneys of aged diabetic mice. This was associated with extensive NF-κB activation. An increase in NF-κB activation has also been shown in tubules and interstitium of diabetic patients with nephropathy. Interestingly, TNFα but not IL-6 mRNA levels were increased in the kidneys of 22 month-old diabetic mice. TNFα is well known as a strong inducer of NF-κB. Since the data showed that TNFα stimulated the expression of MCP-1, RANTES, CXCL-1, MIP-2, iNOS, and VCAM-1 in proximal tubular cells in vitro increased, TNFα may contribute to tubulointerstitial inflammation in 22 month-old mice with diabetes. This postulate is strongly supported by the data herein in that pentosan polysulfate (PPS) treatment of aged diabetic mice resulted in a favorable outcome. One of the postulated mechanisms of PPS actions is to form a protective layer on the surface of bladder epithelium, thereby reducing symptoms due to bladder irritation. PPS largely prevented the pro-inflammatory actions of TNFα in proximal tubular cells, mesangial cells, podocytes, as well as macrophages. Additionally, PPS treatment nearly completely blocked the increase in TNFα mRNA expression, decreased NF-κB activation, and macrophage infiltration in the kidneys of 22 month-old diabetic mice. The PPS-treated aged diabetic mice retained a normal serum creatinine and had less severe glomerular lesions and a largely normal tubulointerstitium. Furthermore, PPS treatment decreased albuminuria and significantly reduced a TNF-α-mediated increase in albumin permeability in podocytes in vitro. Since PPS treatment substantially improves tubulointerstitial lesions in ⅚ nephrectomized rats, PPS may be an additional agent for the treatment of diabetic nephropathy. However, it is important to note that the mechanism by which PPS prevents the increase in thickness of glomerular basement membranes and the decrease in glomerular fenestration in 22 month-old diabetic mice and decreases TNFα expression and TNFα-stimulated albumin permeability is unclear. Furthermore, it is unknown if PPS directly affects oxidative stress and ER stress.

The current study evidences that part of the susceptibility of the aged kidney to increased oxidant stress after the induction of hyperglycemia is due to the pre-existence of increased ROS and inflammation in aging. ER stress may also play a role. Finally, the anti-inflammatory properties of PPS substantially reduces the severity of diabetic nephropathy in 22-month-old mice.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

What is claimed is:

1. A method of treating diabetic nephropathy, comprising: administering to a patient in need thereof, a therapeutically effective dose of pentosan polysulfate (PPS).

2. The method of claim 1, wherein the pentosan polysulfate (PPS) is administered as an oral formulation.

3. The method of claim 1 or 2, wherein the pentosan polysulfate is administered at least once to the patient at fixed, escalating, decreasing doses or combinations thereof.

* * * * *

UNITED STATES PATENT AND TRADEMARK OFFICE
CERTIFICATE OF CORRECTION

PATENT NO. : 8,871,741 B2
APPLICATION NO. : 13/522441
DATED : October 28, 2014
INVENTOR(S) : Gary E. Striker et al.

Page 1 of 1

It is certified that error appears in the above-identified patent and that said Letters Patent is hereby corrected as shown below:

In the Specification

Column 1, Line 17 add the following paragraph:
--GOVERNMENT CLAUSE
This invention was made with government support under R01AG19366-7A1 awarded by The National Institutes of Health. The government has certain rights in the invention.--

Signed and Sealed this
Tenth Day of October, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: oligonucleotide

<400> SEQUENCE: 1
aattaccagc agcaagtgtc c                                              21

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
gggtctgcac agatctcctt                                                20

<210> SEQ ID NO 3
<211> LENGTH: 21
<212> TYPE: DNA
<213> ORGANISM: Artificial Sequence
<220> FEATURE:
<223> OTHER INFORMATION: oligonucleotide

<400> SEQUENCE: 3
ttccctgtca tcgcttgctc t                                              21

<210> SEQ ID NO 4
<211> LENGTH: 20
<212> TYPE: DNA
<213> ORGANISM: Artificial Sequence
<220> FEATURE:
<223> OTHER INFORMATION: oligonucleotide

<400> SEQUENCE: 4
cggatggaga tgccgatttt                                                20

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
cttgaaggtg ttgccctcag                                                20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
aagggagctt cagggtcaag                                                20

<210> SEQ ID NO 7
<211> LENGTH: 20
<212> TYPE: DNA
<213> ORGANISM: Artificial Sequence

```
<220> FEATURE:
<223> OTHER INFORMATION: oligonucleotide

<400> SEQUENCE: 7
tccagagctt gagtgtgacg                                              20

<210> SEQ ID NO 8
<211> LENGTH: 20
<212> TYPE: DNA
<213> ORGANISM: Artificial Sequence
<220> FEATURE:
<223> OTHER INFORMATION: oligonucleotide

<400> SEQUENCE: 8
ttcagggtca aggcaaactt                                              20

<210> SEQ ID NO 9
<211> LENGTH: 21
<212> TYPE: DNA
<213> ORGANISM: Artificial Sequence
<220> FEATURE:
<223> OTHER INFORMATION: oligonucleotide

<400> SEQUENCE: 9
tgctgcagat gctgtgagag t                                            21

<210> SEQ ID NO 10
<211> LENGTH: 21
<212> TYPE: DNA
<213> ORGANISM: Artificial Sequence
<220> FEATURE:
<223> OTHER INFORMATION: oligonucleotide

<400> SEQUENCE: 10
aaaccctcga cccatgtgat c                                            21

<210> SEQ ID NO 11
<211> LENGTH: 20
<212> TYPE: DNA
<213> ORGANISM: Artificial Sequence
<220> FEATURE:
<223> OTHER INFORMATION: oligonucleotide

<400> SEQUENCE: 11
tacgcaccca gagcttttct                                              20

<210> SEQ ID NO 12
<211> LENGTH: 20
<212> TYPE: DNA
<213> ORGANISM: Artificial Sequence
<220> FEATURE:
<223> OTHER INFORMATION: oligonucleotide

<400> SEQUENCE: 12
cttggtcaac cgaacgaagt                                              20

<210> SEQ ID NO 13
<211> LENGTH: 21
<212> TYPE: DNA
<213> ORGANISM: Artificial Sequence
<220> FEATURE:
<223> OTHER INFORMATION: oligonucleotide

<400> SEQUENCE: 13
tactcggggc caaatttgaa g                                            21
```

```
-continued

<210> SEQ ID NO 14
<211> LENGTH: 20
<212> TYPE: DNA
<213> ORGANISM: Artificial Sequence
<220> FEATURE:
<223> OTHER INFORMATION: oligonucleotide

<400> SEQUENCE: 14
catggtagag cggaacaggt                                               20

<210> SEQ ID NO 15
<211> LENGTH: 20
<212> TYPE: DNA
<213> ORGANISM: Artificial Sequence
<220> FEATURE:
<223> OTHER INFORMATION: oligonucleotide

<400> SEQUENCE: 15
tatctcatcc ccaggaaacg                                               20

<210> SEQ ID NO 16
<211> LENGTH: 20
<212> TYPE: DNA
<213> ORGANISM: Artificial Sequence
<220> FEATURE:
<223> OTHER INFORMATION: oligonucleotide

<400> SEQUENCE: 16
ggacgcaggg tcaagagtag                                               20

<210> SEQ ID NO 17
<211> LENGTH: 21
<212> TYPE: DNA
<213> ORGANISM: Artificial Sequence
<220> FEATURE:
<223> OTHER INFORMATION: oligonucleotide

<400> SEQUENCE: 17
gcgacgtgga actggcagaa g                                             21

<210> SEQ ID NO 18
<211> LENGTH: 21
<212> TYPE: DNA
<213> ORGANISM: Artificial Sequence
<220> FEATURE:
<223> OTHER INFORMATION: oligonucleotide

<400> SEQUENCE: 18
ggtacaaccc atcggctggc a                                             21
```